United States Patent
Domschke et al.

[11] Patent Number: 6,043,328
[45] Date of Patent: Mar. 28, 2000

[54] POLYSILOXANE-POLYOL MACROMERS, THEIR PREPARATION AND THEIR USE

[75] Inventors: Angelika Domschke, Lörrach, Germany; Dieter Lohmann, Münchenstein, Switzerland; Jens Höpken, Lörrach, Germany

[73] Assignee: Novartis AG, Basel, Switzerland

[21] Appl. No.: 08/952,416

[22] PCT Filed: May 7, 1996

[86] PCT No.: PCT/EP96/01888

§ 371 Date: Nov. 17, 1997

§ 102(e) Date: Nov. 17, 1997

[87] PCT Pub. No.: WO96/36890

PCT Pub. Date: Nov. 21, 1996

Related U.S. Application Data

[62] Division of application No. 08/569,816, Dec. 8, 1995, Pat. No. 5,760,100.

[30] Foreign Application Priority Data

May 19, 1995 [CH] Switzerland .............. 1496/95

[51] Int. Cl.[7] .............. G02B 1/04; C08G 77/42
[52] U.S. Cl. .............. 526/279; 523/106; 523/107; 525/54.2; 525/326.5; 526/238.2; 526/238.23; 526/301; 526/302; 526/304; 528/32
[58] Field of Search .............. 523/106, 107; 528/32; 525/54.2, 326.5; 526/238.2, 238.23, 279, 301, 302, 304

[56] References Cited

U.S. PATENT DOCUMENTS

| | | | |
|---|---|---|---|
| 4,605,712 | 8/1986 | Mueller et al. | 528/32 |
| 5,057,377 | 10/1991 | Karydas et al. | 428/447 |
| 5,391,592 | 2/1995 | Herbrechtsmeier et al. | 523/107 |
| 5,416,132 | 5/1995 | Yokoyama et al. | 523/107 |
| 5,603,774 | 2/1997 | LeBoeuf et al. | 134/1 |
| 5,648,402 | 7/1997 | Nunez et al. | 523/107 |

FOREIGN PATENT DOCUMENTS

| | | |
|---|---|---|
| 0092928A1 | 4/1983 | European Pat. Off. . |
| 0203391A3 | 4/1986 | European Pat. Off. . |
| 0327886A2 | 2/1988 | European Pat. Off. . |
| 0360248A2 | 9/1988 | European Pat. Off. . |
| 0362145A2 | 9/1989 | European Pat. Off. . |
| 0367720A2 | 10/1989 | European Pat. Off. . |
| 0425436A3 | 10/1990 | European Pat. Off. . |
| 0439019A1 | 1/1991 | European Pat. Off. . |
| 0566332A1 | 7/1993 | European Pat. Off. . |
| 0317377A1 | 10/1988 | France . |
| 104988 | 4/1974 | Germany . |
| 3219220 | 5/1982 | Germany . |
| 3641436 | 4/1986 | Germany . |
| 59-82212 | 4/1984 | Japan . |
| 62-68820 | 3/1987 | Japan . |
| 63-139106 | 6/1988 | Japan . |
| 05339087A | 12/1991 | Japan . |
| 2166654 | 5/1986 | United Kingdom . |
| WO8301617 | 5/1983 | WIPO . |

OTHER PUBLICATIONS

Hydrogels Based on Fluorosiloxanes, J. Kunzler, et al., Polymeric Materials Science and Engineering, vol. 72, 1995.

Enzymatic Grafting of Amylose from Poly(dimethysiloxanes), Braunmuhl, Volker, et al., Macromolecules, 1995, pp. 17–24.

European Search Report (Sep. 1996).

Aldrich catalogue, "Polyvinyl Alcohol," Milwaukee, WI, 1992, p. 1040.

*Primary Examiner*—Andrew E. C. Merriam
*Attorney, Agent, or Firm*—R. Scott Meece; Michael U. Lee; Robert J. Gorman, Jr.

[57] ABSTRACT

The present invention describes a polysiloxane-polyol macromer which is uninterrupted or interrupted by a bivalent structural element and furthermore carries at least one polymerizable segment on a polyol segment; a polymer comprising a polymerization product of at least one macromer according to the invention and, if appropriate, of at least one vinylic comonomer; intermediates; processes for the preparation of a macromer and a polymerization product; moldings, contact lenses, corneal implants or biomedical articles of a polymerization product; and furthermore the use of a macromer according to the invention or of a polymer prepared therefrom for coating a substrate.

64 Claims, No Drawings

POLYSILOXANE-POLYOL MACROMERS, THEIR PREPARATION AND THEIR USE

This application is a division of Ser. No. 08/569,816 filed Dec. 8, 1995, now U.S. Pat. No. 5,760,100.

The present invention describes a polysiloxane-polyol macromer which is uninterrupted or interrupted by a bivalent structural element and furthermore carries at least one polymerizable segment on a polyol segment; a polymer comprising a polymerization product of at least one macromer according to the invention and, if appropriate, of at least one vinylic comonomer; intermediates; processes for the preparation of a macromer and a polymerization product; moldings, contact lenses, corneal implants or biomedical articles of a polymerization product; and furthermore the use of a macromer according to the invention or of a polymer prepared therefrom for coating a substrate.

JP 62/068820 and JP 63/139 106 (Kao Corporation) describe a polymer which consists of a polysiloxane which carries at least one primary amino group and via which the polysiloxane is modified with a sugar residue. These modified polysiloxanes are recommended as additives for hair care products.

WO 83/01617 (Minnesota Mining) describes, inter alia, a macromer which is a methacrylic or acrylamidoacyl derivative of a polysiloxane. Such siloxane derivatives are said to be useful as coatings for films.

EP 362 145 (Ciba-Geigy) describes a contact lens which is produced by reaction of a polydialkylsiloxane prepolymer containing terminal isocyanate with a polydialkylsiloxane-di- or -polyalkanol.

R. Stadler et al. (Macromolecules 28, 17–24 (1995)) describe polysiloxanes with pendent gluconamide or maltoheptaonamide groups, their synthesis starting, for example, from the corresponding peracylated N-allylaldonamides, which are added onto an Si—H group of a corresponding polysiloxane by hydrosilylation using a rhodium or platinum catalyst.

Biocompatible polysiloxane-containing polymers are still desired. Polysiloxanes which have, for example, the following specific properties are particularly desirable: toughness, mechanical damping, slow mechanical relaxation, permeability to oxygen and resistance to deposits of proteins, lipids and salts, and a certain hydrophilicity.

The problem described has been achieved with the preparation of polymerizable macromers which contain free hydroxyl groups. Macromers which are built up, for example, from an amino-alkylated polysiloxane which is derivatized with at least one polyol component containing an unsaturated polymerizable side chain are disclosed.

Polymers can be prepared on the one hand from the macromers according to the invention by homopolymerization. The macromers mentioned furthermore can be mixed and polymerized with one or more hydrophilic and/or hydrophobic comonomers. A special property of the macromers according to the invention is that they function as the element which controls microphase separation between selected hydrophilic and hydrophobic components in a crosslinked end product. The hydrophilic/hydrophobic microphase separation is in the region of less than 300 nm. The macromers are preferably crosslinked at the phase boundaries between, for example, an acrylate comonomer on the one hand and an unsaturated polymerizable side chain of polyols bonded to polysiloxane on the other hand, by covalent bonds and additionally by reversible physical interactions, for example hydrogen bridges. These are formed, for example, by numerous amide or urethane groups. The continuous siloxane phase which exists in the phase composite has the effect of producing a surprisingly high permeability to oxygen.

The present invention relates to a macromer comprising at least one section of the formula (I)

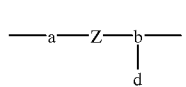

in which (a) is a polysiloxane segment,
(b) is a polyol segment which contains at least 4 C atoms,
Z is a segment (c) or a group $X_1$, in which
segment (c) is defined as $X_2$—R—$X_2$, in which
R is a bivalent radical of an organic compound having up to 20 C atoms and each $X_2$ independently of the other is a bivalent radical which contains at least one carbonyl group, and in which
$X_1$ is defined as $X_2$, and in which
(d) is a radical of the formula (II)

in which $P_1$ is a group which can be polymerized by free radicals;
Y and $X_3$ independently of one another are a bivalent radical which contains at least one carbonyl group;
k is 0 or 1; and
L is a bond or a divalent radical having up to 20 C atoms of an organic compound.

A polysiloxane segment (a) is derived from a compound of the formula (III)

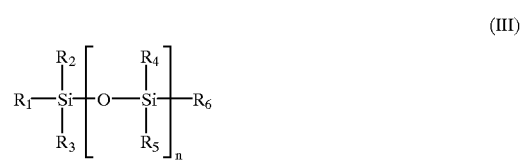

in which n is an integer from 5 to 500;
99.8–25% of the radicals $R_1$, $R_2$, $R_3$, $R_4$, $R_5$ and $R_6$ independently of one another are alkyl and 0.2–75% of the radicals $R_1$, $R_2$, $R_3$, $R_4$, $R_5$ and $R_6$ independently of one another are partly fluorinated alkyl, aminoalkyl, alkenyl, aryl, cyanoalkyl, alk—NH—alk—$NH_2$ or alk—$(OCH_2)_m$—$(OCH_2)_p$—$OR_7$, in which
$R_7$ is hydrogen or lower alkyl,
alk is alkylene, and
m and p independently of one another are an integer from 0 to 10, one molecule containing at least one primary amino or hydroxyl group.

The alkylenoxy groups —$(OCH_2CH_2)_m$ and —$(OCH_2)_p$— in the siloxane of the formula (III) are either distributed randomly in a ligand alk—$(OCH_2CH_2)_m$—$(OCH_2)_p$—$OR_7$ or are distributed as blocks in a chain.

A polysiloxane segment (a) is linked a total of 1–50 times, preferably 2–30 times, and in particular 4–10 times, via a group Z with a segment (b) or another segment (a), Z in an a-Z-a sequence always being a segment (c). The linkage site in a segment (a) with a group Z is an amino or hydroxyl group reduced by one hydrogen.

In a preferred meaning, a polysiloxane segment is derived from a compound of the formula (III) in which
the radicals $R_1$, $R_2$, $R_3$, $R_4$, $R_5$ and $R_6$ are a total of 1–50 times, more preferably 2–30 times, and in particular 4–10 times, independently either terminally or pendently aminoalkyl or hydroxyalkyl, the other variables being as defined above.

In a preferred embodiment, a polysiloxane segment is derived from a compound of the formula (III) in which 95–29% of the radicals $R_1$, $R_2$, $R_3$, $R_4$, $R_5$ and $R_6$ independently of one another are alkyl and 5–71% of the radicals $R_1$, $R_2$, $R_3$, $R_4$, $R_5$ and $R_6$ independently of one another are partly fluorinated alkyl, aminoalkyl, alkenyl, aryl, cyanoalkyl, alk—NH—alk—$NH_2$ or alk—$(OCH_2CH_2)_m$—$(OCH_2)_p$—$OR_7$, and in which the variables are as defined above.

In another preferred embodiment, a polysiloxane segment (a) is derived from a compound of the formula (III) in which 95–29% of the radicals $R_1$, $R_2$, $R_3$, $R_4$, $R_5$ and $R_6$ independently of one another are lower alkyl and 5–71% of the radicals $R_1$, $R_2$, $R_3$, $R_4$, $R_5$ and $R_6$ independently of one another are partly fluorinated alkyl, aminoalkyl or hydroxyalkyl.

In a preferred meaning, n is an integer from 5 to 400, more preferably 10 to 250 and particularly preferably 12 to 125.

In a preferred meaning, the two terminal radicals $R_1$ and $R_6$ are aminoalkyl or hydroxyalkyl, the other variables being as defined above.

In another preferred meaning, the radicals $R_4$ and $R_5$ are 1–50 times, more preferably 2–30 times and in particular 4–10 times pendently aminoalkyl or hydroxyalkyl and the other variables are as defined above.

In another preferred meaning, the radicals $R_1$, $R_2$, $R_3$, $R_4$, $R_5$ and $R_6$ are a total of 1–50 times, more preferably 2–30 times and in particular 4–10 times, independently both terminally and pendently aminoalkyl or hydroxyalkyl and the other variables are as defined above.

If Z is $X_1$, $X_1$ is a bivalent group which contains at least one carbonyl group. A carbonyl group mentioned is flanked in any manner, if appropriate, by —O—, —CONH—, —NHCO— or —NH—. Examples of bivalent groups Z are typically carbonyls, esters, amides, urethanes, ureas or carbonates. XI is preferably an ester, amide, urethane or urea group, in particular an ester or amide group.

$X_2$ is defined in the same way as $X_1$ and is preferably an ester, amide, urethane, carbonate or urea group, more preferably an ester, amide, urethane or urea group and in particular an amide, urethane or urea group.

If Z in formula (I) is $X_1$, a polyol segment (b) is preferably understood as meaning a polyol derived from a carbohydrate, carbohydrate monolactone or carbohydrate dilactone.

A carbohydrate is understood as meaning a mono-, di-, tri-, tetra-, oligo- or polysaccharide. A carbohydrate lactone is understood as meaning the lactone of an aldonic or uronic acid. An aldonic or uronic acid is, for example, a carboxylic acid formed by oxidation of a mono-, di-, tri-, tetra-, oligo- or polysaccharide. Examples of aldonic acid lactones are gluconolactone, galactonolactone, lactobionolactone or maltoheptaonolactone; examples of uronic acid lactones are glucuronic acid lactone, mannuronic acid lactone or iduronic acid lactone. An example of a carbohydrate dilactone is D-glucaro-1,4:6,3-dilactone.

A carbohydrate lactone reacts, for example, with a primary amino group or a hydroxyl group of segment (a) to form a covalent amide or ester bond of the type $X_1$. Such linkages are the constituent of a further preferred embodiment of macromers according to the invention. Such macromers have an alternating distribution of segments of type (a) and (b) which are interrupted by $X_1$.

A preferred embodiment is a macromer comprising at least one section of the formula (I)

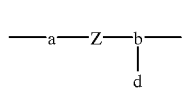

(I)

in which (a) is derived from a compound of the formula (III) in which 95–29% of the radicals $R_1$, $R_2$, $R_3$, $R_4$, $R_5$ and $R_6$ independently of one another are lower alkyl, 5–71% of the radicals $R_1$, $R_2$, $R_3$, $R_4$, $R_5$ and $R_6$ independently of one another are partly fluorinated alkyl, aminoalkyl or hydroxyalkyl, and n is an integer from 5 to 400;

a polyol segment (b) is derived from a polyol, carbohydrate, carbohydrate monolactone or carbohydrate dilactone, with the provisio that segment (b) is derived from a polyol which carries no lactone group if the group Z is a segment (c);

Z is a segment (c) or $X_1$, wherein $X_1$ is an ester, amide, urethane or urea group, and wherein segment (c) represents $X_2$—R—$X_2$, in which R is alkylene, arylene, alkylenearylene or arylenealkylene having up to 14 carbon atoms, or a saturated bivalent cycloaliphatic group having 6 to 14 carbon atoms, and $X_2$ is an amide, urethane or urea group; and (d) is a radical of the formula (II), wherein $P_1$ is alkenyl, $X_3$ is an ester, amide, urethane or urea group, Y is a carbonyl, ester or amide group, k is 0 or 1, and L is a bond or alkylene.

The invention preferably relates to a macromer of the formula (IV)

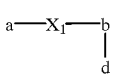

(IV)

in which the variables are as defined above.

The invention furthermore preferably relates to a macromer according to formula (V),

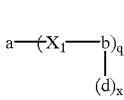

(V)

in which the polysiloxane segment (a) contains q pendent ligands and in which x is 0, 1 or 2, q has an average numerical value of 1–20, preferably 1–10, and in particular 1–5, and in which the segments (b) in a macromer according to the formula (V) are linked in total (per molecule) with up to 20, preferably with up to 15, and in particular with up to 6 polymerizable segments (d).

The invention furthermore preferably relates to a macromer according to formula (VI)

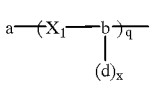

(VI)

in which a linear sequence is present, in which x is 0, or 2, q has an average numerical value of 1–20, preferably 1–10, and in particular 1–5, and in which the segments (b) in a macromer according to the formula (VI) are linked in total (per molecule) with up to 20, preferably with up to 15, and in particular with up to 6 polymerizable segments (d).

The invention furthermore very preferably relates to a macromer according to formula (VII))

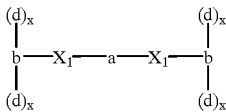

(VII)

in which x is 0, 1 or 2, and the average number of segments (d) per molecule of the formula (VII) is preferably in the range from 2 to 5, and very preferably is in the range from 3 to 4.

More preferred are macromers of formula IV, V, VI or VII, wherein the variables are defined as follows:

a polysiloxane segment (a) is derived from a compound of the formula (III) in which 95–29% of the radicals $R_1$, $R_2$, $R_3$, $R_4$, $R_5$ and $R_6$ independently of one another are lower alkyl, 5–71% of the radicals $R_1$, $R_2$, $R_3$, $R_4$, $R_5$ and $R_6$ independently of one another are partly fluorinated alkyl, aminoalkyl or hydroxyalkyl, and n is an integer from 5 to 400;

a polyol segment (b) is derived from a carbohydrate, carbohydrate monolactone or carbohydrate dilactone;

(d) is a radical of the formula (II): $X_3$—L—$(Y)_k$—$P_1$, in which $P_1$ is alkenyl, $X_3$ is a urethane or urea group, Y is a carbonyl, ester or amide group, k is 0 or 1, and L is a bond or alkylene; and $X_1$ is an ester, amide, urethane or urea group.

More preferred are also macromers of formula IV, V, VI or VII, wherein the variables are defined as follows:

a polysiloxane segment (a) is derived from a compound of the formula (III) in which 95–29% of the radicals $R_1$, $R_2$, $R_3$, $R_4$, $R_5$ and $R_6$ independently of one another are lower alkyl, 5–71% of the radicals $R_1$, $R_2$, $R_3$, $R_4$, $R_5$ and $R_6$ independently of one another are partly fluorinated lower alkyl, lower aminoalkyl or lower hydroxyalkyl, and n is an integer from 10 to 250;

a polyol segment (b) is derived from a carbohydrate, carbohydrate monolactone or carbohydrate dilactone;

(d) is a radical of the formula (II): $X_3$—L—$(Y)_k$—$P_1$, in which $P_1$ is lower alkenyl, $X_3$ is a urethane or urea group, Y is a carbonyl, ester or amide group, k is 0 or 1, and L is a bond or lower alkylene; and $X_1$ is an ester, amide, urethane or urea group.

A polyol segment (b) is derived from a polyol which carries no lactone group if the group Z is a segment (c). Examples of such polyols are a 1,2-polyol, for example the reduced monosaccharides, for example mannitol, glucitol, sorbitol or iditol, a 1,3-polyol, for example polyvinyl alcohol (PVA), which is derived from partly or completely hydrolysed polyvinyl acetate, and furthermore aminoterminal PVA telomers, aminopolyols, aminocyclodextrins, aminomono-, -di-, -tri-, -oligo- or -polysaccharides or cyclodextrin derivatives, for example hydroxypropylcyclodextrin. An abovementioned carbohydrate dilactone can be reacted, for example, with preferably 2 equivalents of an amino-terminal PVA telomer to give a polyol macromer which carries, in the central part, the carbohydrate compound derived from the dilactone. Such polyols of this composition are likewise understood to be a suitable polyol.

As illustrated in formula (I), a segment (b) carries at least one vinylic polymerizable segment (d), wherein the linkage of a segment (d) to a segment (b) is intended via the bivalent radical $X_3$ contained in a segment (d) to an amino and/or hydroxyl group minus a hydrogen atom preferably contained in the polyol-segment (b).

A vinylic polymerizable segment (d) is incorporated either terminally or pendently preferably 1–20 times, more preferably 2–15 times, and in particular 2–6 times, per macromer molecule according to the invention.

A vinylic polymerizable segment (d) is incorporated terminally and also pendently as desired (as a terminal/pendent mixture) preferably 1–20 times, more preferably 2–15 times and in particular 2–6 times, per macromer molecule according to the invention.

A group $P_1$ which can be polymerized by free radicals is, for example, alkenyl, alkenylaryl or alkenylarylenealkyl having up to 20 C atoms. Examples of alkenyl are vinyl, allyl, 1-propen-2-yl, 1-buten-2- or -3- or -4-yl, 2-buten-3-yl and the isomers of pentenyl, hexenyl, octenyl, decenyl or undecenyl. Examples of alkenylaryl are vinylphenyl, vinylnaphthyl or allylphenyl. An example of alkenylarylenealkyl is vinylbenzyl.

$P_1$ is preferably alkenyl or alkenylaryl having up to 12 C atoms, more preferably alkenyl having up to 8 C atoms and in particular alkenyl having up to 4 C atoms.

L is preferably alkylene, arylene, a saturated bivalent cycloaliphatic group having 6 to 20 carbon atoms, arylenealkylene, alkylenearylene, alkylenearylenealkylene or arylenealkylenearylene.

In a preferred meaning, L furthermore is preferably a bond.

In a preferred meaning, L is a divalent radical having up to 12 C atoms, and more preferably a divalent radical having up to 8 C atoms. In a preferred meaning, L furthermore is alkylene or arylene having up to 12 C atoms. A very preferred meaning of L is lower alkylene, in particular lower alkylene having up to 4 C atoms.

Y is preferably a carbonyl, ester, amide or urethane group, in particular a carbonyl, ester or amide group, and very preferably a carbonyl group.

In another preferred meaning, Y is absent, i.e. k is 0.

In a preferred meaning, $X_3$ is a urethane, urea, ester, amide or carbonate group, more preferably a urethane, urea, ester or amide group, and in particular a urethane or urea group.

A vinylic polymerizable segment (d) is derived, for example, from acrylic acid, methacrylic acid, methacryloyl chloride, 2-isocyanatoethyl methacrylate (IEM), allyl isocyanate, vinyl isocyanate, the isomeric vinylbenzyl isocyanates or adducts of hydroxyethyl methacrylate (HEMA) and 2,4-tolylene diisocyanate (TDI) or isophorone diisocyanate (IPDI), in particular the 1:1 adduct.

The invention furthermore preferably relates to a macromer in which a segment (d) is incorporated either terminally or pendently or as a terminal/pendent mixture 5 times.

The invention furthermore preferably relates to a macromer in which a segment (d) is incorporated terminally 5 times.

The diradical R is, for example, alkylene, arylene, alkylenearylene, arylenealkylene or arylenealkylenearylene having up to 20 carbon atoms, a saturated bivalent cycloaliphatic group having 6 to 20 carbon atoms or cycloalkylenealkylenecycloalkylene having 7 to 20 carbon atoms.

In a preferred meaning, R is alkylene, arylene, alkylenearylene, arylenealkylene or arylenealkylenearylene having up to 14 carbon atoms or a saturated bivalent cycloaliphatic group having 6 to 14 carbon atoms.

In a preferred meaning, R is alkylene, arylene, alkylenearylene or arylenealkylene having up to 14 carbon atoms, or a saturated bivalent cycloaliphatic group having 6 to 14 carbon atoms.

In a preferred meaning, R is alkylene or arylene having up to 12 carbon atoms, or a saturated bivalent cycloaliphatic group having 6 to 14 carbon atoms.

In a preferred meaning, R is alkylene or arylene having up to 10 carbon atoms, or is a saturated bivalent cycloaliphatic group having 6 to 10 carbon atoms.

In a very preferred meaning, a segment (c) is derived from a diisocyanate, for example from hexane 1,6-diisocyanate, 2,2,4-trimethylhexane 1,6-diisocyanate, tetramethylene diisocyanate, phenylene 1,4-diisocyanate, toluene 2,4-diisocyanate, toluene 2,6-diisocyanate, m- or p-tetramethylxylene diisocyanate, isophorone diisocyanate or cyclohexane 1,4-diisocyanate.

A preferred embodiment of segment (c) is furthermore derived from a diisocyanate in which the isocyanate groups have different reactivities. The different reactivity is influenced, in particular, by the steric requirements and/or electron density in the neighbourhood of an isocyanate group.

The average molecular weight of a macromer according to the invention is preferably in the range from about 300 to about 30,000, very preferably in the range from about 500 to about 20,000, more preferably in the range from about 800 to about 12,000, and particularly preferably in the range from about 1000 to about 10,000.

A preferred embodiment of the macromer has a segment sequence of the formula (VII)

in which r is an integer from 1 to 10, preferably from 1 to 7, and in particular from 1 to 3;
t is 0 or 1, and preferably 1;
in which a linear (c-a) chain which may or may not be terminated by a segment (b) is present (t=1);
and the above preferences apply to the total number of segments (d), which are preferably bonded to a segment (b).

A preferred embodiment of the macromer has a segment sequence of formula (IX)

in which the sequence (c-a)-(Z-b)$_t$ hangs pendently r times on the segment (a) and may or may not be terminated by a segment (b);
in which r is an integer from 1 to 10, preferably from 1 to 7, and in particular from 1 to 3;
t is 0 or 1, and is preferably 1;
Z is a segment (c) or a group $X_1$;
and the above preferences apply to the total number of segments (d), which are preferably bonded to a segment (b).

Another preferred embodiment of the macromer has a segment sequence of formula (X)

in which s is an integer from 1 to 10, preferably from 1 to 7, and in particular from 1 to 3;
B is a segment (a) or (b);
and the above preferences apply to the number of segments (d), which are bonded to a segment (b).

Another preferred embodiment of the macromer has a segment sequence of the formula (XI)

the structures being linear, and in which
s is an integer from 1 to 10, preferably from 1 to 7, and in particular from 1 to 3;
B is a segment (a) or (b);
t is 0 or 1,
and the above preferences apply to the number of segments (d), which are bonded to a segment (b).

A more preferred embodiment of a macromer is a segment sequence of the formula (VIX), (IX), (X) or (XI) wherein the variables are defined as follows: a polysiloxane segment (a) is derived from a compound of the formula (III) in which 95–29% of the radicals $R_1$, $R_2$, $R_3$, $R_4$, $R_5$ and $R_6$ independently of one another are lower alkyl, 5–71% of the radicals $R_1$, $R_2$, $R_3$, $R_4$, $R_5$ and $R_6$ independently of one another are partly fluorinated alkyl, aminoalkyl or hydroxyalkyl, and n is an integer from 5 to 400; a polyol segment (b) is derived from a polyol, carbohydrate, carbohydrate monolactone or carbohydrate dilactone, with the provisio that segment (b) is derived from a polyol which carries no lactone group if the group Z is a segment (c);
Z is a segment (c) or $X_1$, wherein $X_1$ is an ester, amide, urethane or urea group, and wherein segment (c) represents $X_2$—R—$X_2$, in which R is alkylene, arylene, alkylenearylene or arylenealkylene having up to 14 carbon atoms, or a saturated bivalent cycloaliphatic group having 6 to 14 carbon atoms, and $X_2$ is an amide, urethane or urea group;
(B) is a segment (a) or a segment (b) with the above mentioned preferred definitions; and (d) is a radical of the formula (II): $X_3$—L—$(Y)_k$—$P_1$, which is up to 15 times, even more preferably up to 6 times terminally and/or pendently attached to a segment (b), and wherein $P_1$ is alkenyl, $X_3$ is a ester, amide, urethane or urea group, Y is a carbonyl, ester or amide group, k is 0 or 1, and L is a bond or alkylene.

Another more preferred embodiment of a macromer is a segment sequence of the formula (VIII), (IX), (X) or (XI) wherein the variables are defined as follows:
a polysiloxane segment (a) is derived from a compound of the formula (III) in which 95–29% of the radicals $R_1$, $R_2$, $R_3$, $R_4$, $R_5$ and $R_6$ independently of one another are lower alkyl, 5–71% of the radicals $R_1$, $R_2$, $R_3$, $R_4$, $R_5$ and $R_6$ independently of one another are partly fluorinated lower alkyl, lower aminoalkyl or lower hydroxyalkyl, and n is an integer from 10 to 250;
a polyol segment (b) is derived from a polyol, carbohydrate, carbohydrate monolactone or carbohydrate dilactone, with the provisio that segment (b) is derived from a polyol which carries no lactone group if the group Z is a segment (c);
Z is a segment (c) or $X_1$, wherein $X_1$ is an ester, amide, urethane or urea group, and wherein segment (c) represents $X_2$—R—$X_2$, in which R is alkylene or arylene having up to 14 carbon atoms, or a saturated bivalent cycloaliphatic group having 6 to 14 carbon atoms, and $X_2$ is an amide, urethane or urea group;
(B) is a segment (a) or a segment (b) with the above mentioned preferred definitions; and (d) is a radical of the formula (II): $X_3$—L—$(Y)_k$—$P_1$, which is up to 6 times terminally and/or pendently attached to a segment (b), and wherein $P_1$ is lower alkenyl, $X_3$ is a ester, amide, urethane or urea group, Y is a carbonyl, ester or amide group, k is 0 or 1, and L is a bond or lower alkylene.

The ratio of the number of segments (a) and (b) in a macromer according to the invention is preferably in a range of (a):(b)=3:4, 2:3, 1:2, 1:1, 1:3 or 1:4.

The total sum of segments (a) and (b) or, where appropriate, (a) and (b) and (c) is in a range from 2 to 50, preferably 3 to 30, and in particular in the range from 3 to 12.

Alkyl has up to 20 carbon atoms and can be straight-chain or branched. Suitable examples include dodecyl, octyl, hexyl, pentyl, butyl, propyl, ethyl, methyl, 2-propyl, 2-butyl or 3-pentyl.

Arylene is preferably phenylene or naphthylene, which is unsubstituted or substituted by lower alkyl or lower alkoxy, in particular 1,3-phenylene, 1,4-phenylene or methyl-1,4-phenylene; or 1,5-naphthylene or 1,8-naphthylene.

Aryl is a carbocyclic aromatic radical, which is unsubstituted or substituted by preferably lower alkyl or lower alkoxy. Examples are phenyl, toluyl, xylyl, methoxyphenyl, t-butoxyphenyl, naphthyl or phenanthryl.

A saturated bivalent cycloaliphatic group is preferably cycloalkylene, for example cyclohexylene or cyclohexylene-lower alkylene, for example cyclohexylenemethylene, which is unsubstituted or substituted by one or more lower alkyl groups, for example methyl groups, for example trimethylcyclohexylenemethylene, for example the bivalent isophorone radical.

The term "lower" in the context of this invention in connection with radicals and compounds, unless defined otherwise, means, in particular, radicals or compounds having up to 8 carbon atoms, preferably having up to 4 carbon atoms.

Lower alkyl has, in particular, up to 8 carbon atoms, preferably up to 4 carbon atoms, and is, for example, methyl, ethyl, propyl, butyl, tert-butyl, pentyl, hexyl or isohexyl.

Alkylene has up to 12 carbon atoms and can be straight-chain or branched. Suitable examples include decylene, octylene, hexylene, pentylene, butylene, propylene, ethylene, methylene, 2-propylene, 2-butylene or 3-pentylene.

Lower alkylene is alkylene having up to 8, and particularly preferably having up to 4 carbon atoms. A particularly preferred meaning of lower alkylene is propylene, ethylene or methylene.

The arylene unit of alkylenearylene or arylenealkylene is preferably phenylene, which is unsubstituted or substituted by lower alkyl or lower alkoxy, and the alkylene unit of this is preferably lower alkylene, such as methylene or ethylene, in particular methylene. Such radicals are therefore preferably phenylenemethylene or methylenephenylene.

Lower alkoxy has, in particular, up to 8 carbon atoms, preferably up to 4 carbon atoms, and is, for example, methoxy, ethoxy, propoxy, butoxy, tert-butoxy or hexyloxy.

Partly fluorinated alkyl is understood as meaning alkyl in which up to 90%, preferably up to 70%, and in particular up to 50%, of the hydrogens are replaced by fluorine.

Arylenealkylenearylene is preferably phenylene-lower alkylene-phenylene having up to 8, and in particular having up to 4 carbon atoms in the alkylene unit, for example phenylenethylenephenylene or phenylenemethylenephenylene.

A monosaccharide in the context of the present invention is understood as meaning an aldopentose, aldohexose, aldotetrose, ketopentose or ketohexose.

Examples of an aldopentose are D-ribose, D-arabinose, D-xylose or D-lyose; examples of an aldohexose are D-allose, D-altrose, D-glucose, D-mannose, D-gulose, D-idose, D-galactose, D-talose, L-fucose or L-rhamnose; examples of a ketopentose are D-ribulose or D-xylulose; examples of a tetrose are D-erythrose or threose; and examples of a ketohexose are D-psicose, D-fructose, D-sorbose or D-tagatose.

Examples of a disaccharide are trehalose, maltose, isomaltose, cellobiose, gentiobiose, saccharose, lactose, chitobiose, N,N-diacetylchitobiose, palatinose or sucrose.

Raffinose, panose or maltotriose may be mentioned as an example of a trisaccharide.

Examples of an oligosaccharide are maltotetraose, maltohexaose, chitoheptaose and furthermore cyclic oligosaccharides, such as cyclodextrins.

Cyclodextins contain 6 to 8 identical units of α-1,4-glucose. Some examples are α-, β-and γ-cyclodextrin, derivatives of such cyclodextrins, for example hydroxypropylcyclodextrins, and branched cyclodextrins.

The macromers according to the invention can be prepared by processes known per se, for example as follows.

In a first step, a polysiloxane containing e.g. at least one primary amino- or hydroxyalkyl group is reacted with a carbohydrate lactone, an amide or ester bond being formed and a compound of the formula (XIIa) or (XIIb) being formed

(XIIa)

(XIIb)

in which the variables are as defined above and

Z is a group $X_1$, after which the compound (XII) is reacted with an unsaturated polymerizable compound of the formula (XIII)

(XIII)

in which $X_4$ is a group which is coreactive with a hydroxyl or amino group of segment (b), an $X_3$ group of a segment (d) according to formula (II) being formed from such a reaction, and in which $X_4$ is preferably —COOH, —COOR$_{10}$, —COCl or —NCO, in which $R_{10}$ is alkyl, or is aryl which is unsubstituted or substituted by lower alkyl or lower alkoxy, and the other variables are as defined above, after which a macromer according to the formula (IV) or (V) is formed

(IV)

(V)

in which the segments (d) are incorporated terminally and/or pendently.

Another process starts from a polysiloxane (a) which contains terminal primary amino- or hydroxyalkyl groups and is reacted with a carbohydrate dilactone to form linear structures of the formula

(XIV)

in which the variables are as defined and preferred above, after which a compound of the formula (XIV) is reacted with a compound of the formula (XIII) analogously to the above process to give a macromer of the formula (VI)

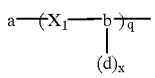 (VI)

in which the variables are as defined and preferred above.

Another process starts from a polysiloxane (a) which contains terminal primary amino- or hydroxyalkyl groups and is initially reacted with a bifunctional compound of the formula (XV)

$$X_4-R-X_4 \quad (XV)$$

in which $X_4$ is a group which is coreactive with a hydroxyl or amino group of segment (a), an $X_2$ group of a segment (c) being formed from such a reaction,
and in which
$X_4$ is preferably —COOH, —COOR$_{10}$, —COCl or —NCO,
in which $R_{10}$ is alkyl, or aryl which is unsubstituted or substituted by lower alkyl or lower alkoxy, and
R is as defined above,
after which this intermediate is reacted with a polyol which carries no lactone group to give a compound of the formula (XVI)

$$b\text{-}c\text{-}\{a\text{-}c\}_s\text{-}b \quad (XVI)$$

in which the variables are as defined and preferred above, after which the compound of the formula (XVI) is reacted with a compound of the formula (XIII) to give a macromer of the formula (X), (segments (d) not shown in formula (X)), $$b\text{-}c\text{-}\{a\text{-}c\}_s\text{-}B \quad (X)$$

in which s is an integer from 1 to 10, preferably from 1 to 7, and in particular from 1 to 3;
B is a segment (a) or (b);
and the above preferences apply to the number of segments (d) which are bonded to a segment (b).

Another process starts from a bifunctional compound of the formula (XV)

$$X_4-R-X_4 \quad (XV)$$

which is reacted with an excess of polysiloxane (a) to give an -a-(c-a)$_r$- sequence, in which the above meanings apply, after which, in a second step, the intermediate is reacted with a polyol which carries no lactone to give a compound of the formula (XVII)

$$b\text{-}Z\text{-}a\text{-}\{c\text{-}a\}_r\text{-}Z\text{-}b \quad (XVII)$$

after which the compound (XVII) is reacted with the compound (XIII) to give a macromer of the formula (VIII), (segments (d) not shown in formula (VIII)), $$b\text{-}Z\text{-}a\text{-}\{c\text{-}a\}_r\text{-}(Z\text{-}b)_t \quad (VIII)$$

in which r is an integer from 1 to 10, preferably from 1 to 7, and in particular from 1 to 3;
t is 0 or 1, and is preferably 1;
in which a linear (c-a) chain, which may or may not be terminated by a segment (b), is present (t=1);
and the above preferences apply to the total number of segments (d), which are preferably bonded to a segment (b).

Another process starts from a carbohydrate lactone which is reacted in a first step with a compound of the formula (XIII), the lactone function being retained, after which the intermediate is reacted with a polysiloxane containing at least one amino or hydroxyl group to give a compound of the formula (IV) or (V)

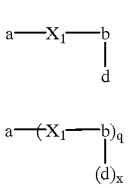

(IV)

(V)

in which q is typically 1 or 2,
and in which the above meanings and preferences otherwise apply, and the segments (d) are incorporated terminally and/or pendently.

The present invention furthermore relates to the intermediates which are novel and which occur during synthesis of the macromers according to the invention.

The invention therefore furthermore relates to a compound of the formula (XIIa)

$$(a\text{-}Z\text{-}b)_q \quad (XIIa)$$

in which q is greater than 1,
(a) is derived from a polysiloxane as defined in the main claim and
(b) is derived from a carbohydrate dilactone.

The invention furthermore relates to a compound of the formula (XIIb)

$$a\text{-}(Z\text{-}b)_q \quad (XIIb)$$

in which Z, (b) and q are as defined and preferred above, but with the proviso that a segment (a) is derived from a compound of the formula (III)

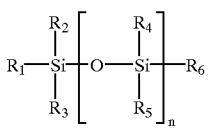

(III)

in which n is an integer from 5 to 500;
99.8–25% of the radicals $R_1$, $R_2$, $R_3$, $R_4$, $R_5$ and $R_6$ independently of one another are alkyl and 0.2–75% of the radicals $R_1$, $R_2$, $R_3$, $R_4$, $R_5$ and $R_6$ independently of one another are partly fluorinated alkyl, aminoalkyl, alkenyl, aryl, cyanoalkyl, alk—NH—Alk—NH$_2$ or alk—(OCH$_2$CH$_2$)$_m$—(OCH$_2$)$_p$—OR$_7$ in which
$R_7$ is hydrogen or lower alkyl,
alk is alkylene and
m and p independently of one another are an integer from 0 to 10,
one molecule containing at least one primary amino or hydroxyl group and at least one partly fluorinated alkyl group.

The invention furthermore relates to a compound of the formula (XVI)

$$b\text{-}c\text{-}\{a\text{-}c\}_s\text{-}b \quad (XVI)$$

in which a segment (b) is derived from a polyol which carries no lactone
and the other variables are as defined and preferred above.

The invention furthermore relates to a compound of the formula (XVII)

b-Z-a-{c-a}$_r$-Z-b     (XVII)

in which a segment (b) is derived from a polyol which carries no lactone
and the other variables are as defined and preferred above.

A siloxane (a) containing at least one primary amino or hydroxyl group is, for example, commercially obtainable. Examples are KF-6002, KF-8003, X-22–161C (Shin Etsu) or GP4 (Genesee). Other siloxanes can be synthesized with the aid of published processes.

A polyol (b) required for the synthesis is as a rule commercially obtainable. Examples are gluconolactone or lactobionolactone. Otherwise, they can be synthesized with the aid of a published process.

The compounds according to the invention can be prepared in the presence or absence of a solvent. A solvent which is largely inert, i.e. does not participate in the reaction, is advantageously used. Suitable examples of these are ethers, such as tetrahydrofuran (THF), 1,2-dimethoxyethane, diethylene glycol dimethyl ether or dioxane, halogenated hydrocarbons, such as chloroform or methylene chloride, bipolar aprotic solvents, such as acetonitrile, acetone, dimethylformamide (DMF) or dimethyl sulfoxide (DMSO), hydrocarbons, such as toluene or xylene, and furthermore pyridine or N-methylmorpholine.

The reactants are advantageously employed in stoichiometric amounts for the preparation of the compounds according to the invention. The reaction temperature can be, for example, from −30° C. to 150° C. The range from 0° C. to 40° C. is a preferred temperature range. The reaction times here are in the range from about 15 minutes to 7 days, preferably in the region of about 12 hours. If necessary, the reaction is carried out under argon or nitrogen as an inert gas. A suitable catalyst is advantageously added for urethane-forming reactions, for example dibutyltin dilaurate (DBTDL).

The present invention furthermore relates to a polymer comprising a polymerization product of at least one macromer according to the invention as defined above and, if appropriate, at least one vinylic comonomer (a).

The preferred composition of a polymer according to the invention comprises a weight content, with respect to the total polymer, of a macromer according to the invention in the range from 100 to 0.5%, in particular in the range from 80 to 10%, and preferably in the range from 70 to 30%.

In a preferred polymer comprising a polymerization product of at least one macromer according to the invention, comonomer (a) is absent and the polymer is preferably a homopolymer.

A comonomer (a) which is contained in a polymer according to the invention can by hydrophilic or hydrophobic or a mixture of both. Suitable comonomers include, in particular, those which are usually used for the preparation of contact lenses and biomedical materials.

A hydrophobic comonomer (a) is understood as meaning monomers which typically give, as a homopolymer, polymers which are water-insoluble and can absorb less than 10% by weight of water.

Analogously, a hydrophilic comonomer (a) is understood as meaning a monomer which typically gives, as a homopolymer, a polymer which is water-soluble or can absorb at least 10% by weight of water.

Suitable hydrophobic comonomers (a) include, without this list being conclusive, $C_1$–$C_{18}$alkyl and $C_3$–$C_{18}$cycloalkyl acrylates and methacrylates, $C_3$–$C_{18}$alkylacrylamides and -methacrylamides, acrylonitrile, methacrylonitrile, vinyl $C_1$–$C_{18}$alkanoates, $C_2$–$C_{18}$alkenes, $C_2$–$C_{18}$haloalkenes, styrene, lower alkyl styrene, lower alkyl vinyl ethers, $C_2$–$C_{10}$perfluoroalkyl acrylates and methacrylates or correspondingly partly fluorinated acrylates and methacrylates, $C_3$–$C_{12}$perfluoroalkyl-ethyl-thiocarbonylaminoethyl acrylates and methacrylates, acryloxy- and methacryloxy-alkylsiloxanes, N-vinylcarbazole and $C_1$–$C_{12}$alkyl esters of maleic acid, fumaric acid, itaconic acid, mesaconic acid and the like. Preferred comonomers are, for example, acrylonitrile, $C_1$–$C_4$alkyl esters of vinylically unsaturated carboxylic acids having 3 to 5 carbon atoms, or vinyl esters of carboxylic acids having up to 5 carbon atoms.

Examples of suitable hydrophobic comonomers (a) include methyl acrylate, ethyl acrylate, propyl acrylate, isopropyl acrylate, isobutyl acrylate (IBA), isooctyl acrylate (OA), isodecyl acrylate (DA), cyclohexyl acrylate, 2-ethylhexyl acrylate (EHA), methyl methacrylate, ethyl methacrylate, propyl methacrylate, butyl acrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethylthiocarbonylaminoethyl methacrylate, isobornyl methacrylate, trifluoroethyl methacrylate, hexafluoroisopropyl methacrylate, hexafluorobutyl (meth)acrylate (HFBMA and HFBA), tris-trimethylsilyloxy-silyl-propyl methacrylate (TRIS), 3-methacryloxypropylpentamethyldisiloxane and bis (methacryloxypropyl)-tetramethyldisiloxane.

Preferred examples of hydrophobic comonomers (a) are methyl methacrylate, IBA, HFBA, HFBMA, OA, EHA, DA, TRIS and acrylonitrile.

Suitable hydrophilic comonomers (a) include, without this list being conclusive, hydroxyl-substituted lower alkyl acrylates and methacrylates, acrylamide, methacrylamide, lower alkylacrylamides and -methacrylamides, ethoxylated acrylates and methacrylates, hydroxyl-substituted lower alkylacrylamides and -methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl-4,4'-dialkyloxazolin-5-one, 2- and 4-vinylpyridine, vinylically unsaturated carboxylic acids having a total of 3 to 5 carbon atoms, amino-lower alkyl (where the term "amino" also includes quaternary ammonium), mono-lower alkylamino-lower alkyl and di-lower alkylamino-lower alkyl acrylates and methacrylates, allyl alcohol and the like. Preferred comonomers are, for example, N-vinyl-2-pyrrolidone, acrylamide, methacrylamide, hydroxyl-substituted lower alkyl acrylates and methacrylates, hydroxyl-substituted lower alkylacrylamides and -methacrylamides and vinylically unsaturated carboxylic acids having a total of 3 to 5 carbon atoms.

Examples of suitable hydrophilic comonomers (a) include hydroxyethyl methacrylate (HEMA), hydroxyethyl acrylate, hydroxypropyl acrylate, trimethylammonium-2-hydroxypropyl methacrylate hydrochloride (Blemer®QA, for example from Nippon Oil), dimethylaminoethyl methacrylate (DMAEMA), dimethylaminoethyl methacrylamide, acrylamide, methacrylamide, N,N-dimethylacrylamide (DMA), allyl alcohol, vinylpyridine, glycerol methacrylate, N-(1,1-dimethyl-3-oxobutyl)acrylamide, N-vinyl-2-pyrrolidone (NVP), acrylic acid, methacrylic acid and the like.

Preferred hydrophilic comonomers (a) are 2-hydroxyethyl methacrylate, dimethylaminoethyl methacrylate, trimethylammonium-2-hydroxypropyl methacrylate hydrochloride, N,N-dimethylacrylamide and N-vinyl-2-pyrrolidone.

The polymers according to the invention are built up in a manner known per se from the corresponding monomers (the term monomers here also including a macromer according to the invention) by a polymerization reaction with which the expert is familiar. Usually, a mixture of the abovementioned monomers is heated, with the addition of an agent which forms free radicals. Such an agent which forms free radicals is, for example, azoisobutyronitrile (AIBN), potassium peroxodisulfate, dibenzoyl peroxide, hydrogen peroxide or sodium percarbonate. If the compounds mentioned are heated, for example, free radicals are then formed, by homolysis, and can then, for example, initiate a polymerization.

A polymerization reaction can particularly preferably be carried out using a photoinitiator. Photopolymerization is the term used in this case. For photopolymerization, a photoinitiator which can initiate free radical polymerization and/or crosslinking by the use of light is suitably added. Examples of this are familiar to the expert, and specifically, suitable photoinitiators are benzoin methyl ether, 1-hydroxycyclohexyl phenyl ketone and Darocur and Irgacur types, preferably Darocur 1173® and Darocur 2959®. Reactive photoinitiators which can be incorporated, for example, into a macromer or can be used as a special comonomer (a) are also suitable. Examples of these are to be found in EP 632 329. The photopolymerization can then be triggered off by actinic radiation, for example light, in particular UV light of a suitable wavelength. The spectral requirements can be controlled accordingly, if appropriate, by addition of suitable photosensitizers.

A polymerization can be carried out in the presence or absence of a solvent. Suitable solvents are in principle all solvents which dissolve the monomers used, for example water, alcohols, such as lower alkanols, for example ethanol or methanol, and furthermore carboxylic acid amides, such as dimethylformamide, dipolar aprotic solvents, such as dimethyl sulfoxide or methyl ethyl ketone, ketones, for example acetone or cyclohexanone, hydrocarbons, for example toluene, ethers, for example THF, dimethoxyethane or dioxane, and halogenated hydrocarbons, for example trichloroethane, and also mixtures of suitable solvents, for example mixtures of water with an alcohol, for example a water/ethanol or a water/methanol mixture.

A preferred embodiment relates also to a polymer which comprises the polymerization product of the following components in weight percent based on the total weight of the polymer:
(1) 25–45% of a macromer according to the definition of the main claim,
(2) 25–75% of a hydrophobic monomer, and
(3) 15–40% of a hydrophilic monomer.

Another preferred embodiment relates also to a polymer which comprises the polymerization product of the following components in weight percent based on the total weight of the polymer:
(1) 25–45% of a macromer of formula IV, V, VI or VII, wherein the variables are defined as follows:
a polysiloxane segment (a) is derived from a compound of the formula (III) in which 95–29% of the radicals $R_1$, $R_2$, $R_3$, $R_4$, $R_5$ and $R_6$ independently of one another are lower alkyl, 5–71% of the radicals $R_1$, $R_2$, $R_3$, $R_4$, $R_5$ and $R_6$ independently of one another are partly fluorinated alkyl, aminoalkyl or hydroxyalkyl, and n is an integer from 5 to 400;
a polyol segment (b) is derived from a carbohydrate, carbohydrate monolactone or carbohydrate dilactone;
(d) is a radical of the formula (II): $X_3$—L—$(Y)_k$—$P_1$, in which $P_1$ is alkenyl, $X_3$ is a urethane or urea group, Y is a carbonyl, ester or amide group, k is 0 or 1, and L is a bond or alkylene; and
$X_1$ is an ester, amide, urethane or urea group,
(2) 25–75% of a hydrophobic monomer, and
(3) 15–40% of a hydrophilic monomer.

Another preferred embodiment relates also to a polymer which comprises the polymerization product of the following components in weight percent based on the total weight of the polymer:
(1) 30–40% of a macromer of formula IV, V, VI or VII, wherein the variables are defined as follows:
a polysiloxane segment (a) is derived from a compound of the formula (III) in which 95–29% of the radicals $R_1$, $R_2$, $R_3$, $R_4$, $R_5$ and $R_6$ independently of one another are lower alkyl, 5–71% of the radicals $R_1$, $R_2$, $R_3$, $R_4$, $R_5$ and $R_6$ independently of one another are partly fluorinated alkyl, aminoalkyl or hydroxyalkyl, and n is an integer from 5 to 400;
a polyol segment (b) is derived from a carbohydrate, carbohydrate monolactone or carbohydrate dilactone;
(d) is a radical of the formula (II): $X_3$—L—$(Y)_k$—$P_1$, in which $P_1$ is alkenyl, $X_3$ is a urethane or urea group, Y is a carbonyl, ester or amide group, k is 0 or 1, and L is a bond or alkylene; and
$X_1$ is an ester, amide, urethane or urea group,
(2) 30–70% of a hydrophobic monomer, and
(3) 20–35% of a hydrophilic monomer.

Another preferred embodiment relates also to a polymer which comprises the polymerization product of the following components in weight percent based on the total weight of the polymer:
(1) 25–45% of a macromer having the segment sequence in accordance to formula (VIII), (IX), (X) or (XI) wherein the variables are defined as follows:
a polysiloxane segment (a) is derived from a compound of the formula (III) in which 95–29% of the radicals $R_1$, $R_2$, $R_3$, $R_4$, $R_5$ and $R_6$ independently of one another are lower alkyl, 5–71% of the radicals $R_1$, $R_2$, $R_3$, $R_4$, $R_5$ and $R_6$ independently of one another are partly fluorinated alkyl, aminoalkyl or hydroxyalkyl, and n is an integer from 5 to 400;
a polyol segment (b) is derived from a polyol, carbohydrate, carbohydrate monolactone or carbohydrate dilactone, with the proviso that segment (b) is derived from a polyol which carries no lactone group if the group Z is a segment (c);
Z is a segment (c) or $X_1$, wherein $X_1$ is an ester, amide, urethane or urea group, and wherein segment (c) represents $X_2$—R—$X_2$, in which R is alkylene, arylene, alkylenearylene or arylenealkylene having up to 14 carbon atoms, or a saturated bivalent cycloaliphatic group having 6 to 14 carbon atoms, and $X_2$ is an amide, urethane or urea group; (B) is a segment (a) or a segment (b) with the above mentioned preferred definitions; and (d) is a radical of the formula (II): $X_3$—L—$(Y)_k$—$P_1$, which is up to 15 times, even more preferably up to 6 times terminally and/or pendently attached to a segment (b), and wherein $P_1$ is alkenyl, $X_3$ is a ester, amide, urethane or urea group, Y is a carbonyl, ester or amide group, k is 0 or 1, and L is a bond or alkylene,
(2) 25–75% of a hydrophobic monomer, and
(3) 15–40% of a hydrophilic monomer.

If appropriate, a polymer network can be reinforced by addition of a so-called crosslinking agent, for example a polyunsaturated comonomer (b). The invention furthermore relates to a polymer comprising the polymerization product of a macromer according to the invention with, if appropriate, at least one vinylic comonomer (a) and with at least one comonomer (b).

Examples of typical comonomers (b) are, for example, allyl(meth)acrylate, lower alkylene glycol di(meth)acrylate, poly lower alkylene glycol di(meth)acrylate, lower alkylene di(meth)acrylate, divinyl ether, divinyl sulfone, di- or trivinylbenzene, trimethylolpropane tri(meth)acrylate, pentaerythritol tetra(meth)acrylate, bisphenol A di(meth)acrylate, methylenebis(meth)acrylamide, triallyl phthalate or diallyl phthalate.

The amount of comonomer (b) used is expressed in the weight content with respect to the total polymer and is in the range from 20 to 0.05%, in particular in the range from 10 to 0.1%, and preferably in the range from 2 to 0.1%.

The polymers according to the invention can be processed in a manner known per se to give moldings, in particular contact lenses, for example by carrying out the photopolymerization or photocrosslinking of the polymers according to the invention in a suitable contact lens molding. The invention therefore furthermore relates to moldings which essentially comprise polymers according to the invention. Other examples of moldings according to the invention, in addition to contact lenses, are biomedical articles or specifically ophthalmic moldings, for example artificial corneas, intraocular lenses, eye dressings, moldings which can be used in surgery, such as heart valves, artificial arteries or the like, and furthermore coatings, films or membranes, for example membranes for diffusion control, films for information storage which can be photostructured, or photoresist materials, for example membranes or moldings for etch resists or screen printing resists, and furthermore particles, in particular microparticles, capsules, in particular microcapsules, films and plasters for drug delivery systems.

A special embodiment of the invention is directed at contact lenses which include a polymer according to the invention or essentially or completely comprise a polymer according to the invention. Such contact lenses have a range of unusual and extremely advantageous properties. These properties are, for example, their excellent tolerability by the human cornea (if appropriate after a suitable surface treatment (coating)) and by lachrymal fluid, which is based on a balanced relationship between water content, permeability to oxygen and mechanical and adsorptive properties. This results in high comfort, no irritation and no allergenic effects. Because of their favourable permeability properties with respect to various salts, nutrients, water and other diverse components of lachrymal fluid and gases ($CO_2$, $O_2$), contact lenses according to the invention do not or only insignificantly impair the natural metabolic processes in the cornea. In contrast to many other siloxane-containing contact lenses, for example, hydrophilic lenses which comprise a macromer according to the invention as an essential constituent do not display the undesired suction cup effect. Contact lenses according to the invention are specifically suitable for wear over a relatively long period of time (extended wear). Furthermore, the contact lenses according to the invention are of high dimensional stability and storage stability.

Surface treatment as is referred to above, in particular refers to a process to render a surface ophthalmically more compatible, in which, by means of contact with a vapor or liquid, and/or by means of application of an energy source (a) a coating is applied to the surface to an article, (b) chemical species are adsorbed onto the surface of an article, (c) the chemical nature (e.g. electrostatic charge) of chemical groups on the surface of an article are altered, or (d) the surface properties of an article are otherwise modified.

There are a variety of methods disclosed in the art for rendering a surface of a material hydrophilic. For example, the lens may be coated with a layer of a hydrophilic polymeric material. Alternatively, hydrophilic groups may be grafted onto the surface of the lens, thereby producing a monolayer of hydrophilic material. These coating or grafting processes may be effected by a number of processes, including without limitation thereto, exposing the lens to plasma gas or immersing the lens in a monomeric solution under appropriate conditions.

Another set of methods of altering the surface properties of a lens involves treatment prior to polymerization to form the lens. For example, the molding may be treated with plasma (i.e. an ionized gas), a static electrical charge, irradiation, or other energy source, thereby causing the prepolymerization mixture immediately adjacent the molding surface to differ in composition from the core of the prepolymerization mixture.

A preferred class of surface treatment processes are plasma processes, in which an ionized gas is applied to the surface of an article. Plasma gases and processing conditions are described more fully in U.S. Pat. No. 4,312,575 and U.S. Pat. No. 4,632,844, which are incorporated herein by reference. The plasma gas is preferably a mixture of lower alkanes and nitrogen, oxygen or an inert gas.

In a preferred embodiment, the lens is plasma treated in the presence of a mixture of (a) a $C_1$–$C_6$alkane and (b) a gas selected from the group consisting of nitrogen, argon, oxygen, and mixtures thereof. A $C_1$–$C_6$alkane (a) is preferably selected from a $C_1$–$C_4$alkane and may for example be methane, propane or butane. A gas (b) is preferably selected from nitrogen, oxygen and a mixture thereof and in particular from air, wherein air within the meaning of the present invention denotes 79% nitrogen and 21% oxygen. In a more preferred embodiment, the lens is plasma treated in the presence of a mixture of methane and air. The plasma treatment (apparatus and process) as is referred to hereinbefore and hereinafter is preferably carried out in analogy to the disclosure of H. Yasuda, "Plasma Polymerization", Academic Press, Orlando, Fla. (1985), pages 319 forward.

The present invention also relates to a molding comprising one of the novel polymers, wherein the surface of the molding is plasma treated in the presence of a $C_1$–$C_6$alkane (a) and a gas (b) which is selected from the group consisting of nitrogen, argon, oxygen, and mixtures thereof.

A preferred embodiment relates to a molding which comprises the polymer of a polymerization product of the following components in weight percent based on the total weight of the polymer:

(1) 25–45% of a macromer of formula IV, V, VI or VII, wherein the variables are defined as follows:

a polysiloxane segment (a) is derived from a compound of the formula (III) in which 95–29% of the radicals $R_1$, $R_2$, $R_3$, $R_4$, $R_5$ and $R_6$ independently of one another are lower alkyl, 5–71% of the radicals $R_1$, $R_2$, $R_3$, $R_4$, $R_5$ and $R_6$ independently of one another are partly fluorinated alkyl, aminoalkyl or hydroxyalkyl, and n is an integer from 5 to 400; a polyol segment (b) is derived from a carbohydrate, carbohydrate monolactone or carbohydrate dilactone;

(d) is a radical of the formula (II): $X_3$—L—$(Y)_k$—$P_1$, in which $P_1$ is alkenyl, $X_3$ is a urethane or urea group, Y is a carbonyl, ester or amide group, k is 0 or 1, and L is a bond or alkylene; and $X_1$ is an ester, amide, urethane or urea group, (2) 25–75% of a hydrophobic monomer, and
(3) 15–40% of a hydrophilic monomer,
wherein the surface of said molding is plasma treated in the presence of a $C_1$–$C_4$alkane and air.

Another preferred embodiment relates also to a molding which comprises the polymer of a polymerization product of the following components in weight percent based on the total weight of the polymer:

(1) 30–40% of a macromer of formula IV, V, VI or VII, wherein the variables are defined as follows:

a polysiloxane segment (a) is derived from a compound of the formula (III) in which 95–29% of the radicals $R_1$, $R_2$, $R_3$, $R_4$, $R_5$ and $R_6$ independently of one another are lower alkyl, 5–71% of the radicals $R_1$, $R_2$, $R_3$, $R_4$, $R_5$ and $R_6$ independently of one another are partly fluorinated alkyl, aminoalkyl or hydroxyalkyl, and n is an integer from 5 to 400;

a polyol segment (b) is derived from a carbohydrate, carbohydrate monolactone or carbohydrate dilactone;

(d) is a radical of the formula (II): $X_3$—L—$(Y)_k$—$P_1$, in which PI is alkenyl, $X_3$ is a urethane or urea group, Y is a carbonyl, ester or amide group, k is 0 or 1, and L is a bond or alkylene; and $X_1$ is an ester, amide, urethane or urea group,
(2) 30–70% of a hydrophobic monomer, and
(3) 20–35% of a hydrophilic monomer,
wherein the surface of said molding is plasma treated in the presence of a $C_1$–$C_4$alkane and air.

Another preferred embodiment relates also to a molding which comprises the polymer of a polymerization product of the following components in weight percent based on the total weight of the polymer:

(1) 25–45% of a macromer having the segment sequence in accordance to formula (VIII), (IX), (X) or (XI) wherein the variables are defined as follows:

a polysiloxane segment (a) is derived from a compound of the formula (III) in which 95–29% of the radicals $R_1$, $R_2$, $R_3$, $R_4$, $R_5$ and $R_6$ independently of one another are lower alkyl, 5–71% of the radicals $R_1$, $R_2$, $R_3$, $R_4$, $R_5$ and $R_6$ independently of one another are partly fluorinated alkyl, aminoalkyl or hydroxyalkyl, and n is an integer from 5 to 400;

a polyol segment (b) is derived from a polyol, carbohydrate, carbohydrate monolactone or carbohydrate dilactone, with the provisio that segment (b) is derived from a polyol which carries no lactone group if the group Z is a segment (c);

Z is a segment (c) or $X_1$, wherein $X_1$ is an ester, amide, urethane or urea group, and wherein segment (c) represents $X_2$—R—$X_2$, in which R is alkylene, arylene, alkylenearylene or arylenealkylene having up to 14 carbon atoms, or a saturated bivalent cycloaliphatic group having 6 to 14 carbon atoms, and $X_2$ is an amide, urethane or urea group;

(B) is a segment (a) or a segment (b) with the above mentioned preferred definitions; and (d) is a radical of the formula (II): $X_3$—L—$(Y)_k$—$P_1$, which is up to 15 times, even more preferably up to 6 times terminally and/or pendently attached to a segment (b), and wherein $P_1$ is alkenyl, $X_3$ is a ester, amide, urethane or urea group, Y is a carbonyl, ester or amide group, k is 0 or 1, and L is a bond or alkylene, (2) 25–75% of a hydrophobic monomer, and
(3) 15–40% of a hydrophilic monomer, wherein the surface of said molding is plasma treated in the presence of a $C_1$–$C_4$alkane and air.

The present invention furthermore relates to contact lenses which essentially comprise one of the polymers according to the invention, the contact lenses being in particular soft contact lenses which comprise preferably 1–40% of water.

The invention furthermore relates to contact lenses essentially comprising one of the polymers according to the invention, the contact lenses being in particular flexible contact lenses which are permeable to gas and are preferably of low water content (RGP), and may also be hybrid lenses.

All the abovementioned advantages of course apply not only to contact lenses, but also to other moldings according to the invention.

The present invention furthermore relates to the use of a macromer according to the invention or of a polymer or crosslinked polymer prepared therefrom and described above for coating a base material, for example glass, ceramic or metal, and preferably polymer substrates, for example products which can be used ophthalmically, such as contact lenses, intraoccular lenses or eye dressings, as well as products which can be used medically, for example in surgical or pharmaceutical systems, hydrophilic coatings being preferred in the cases mentioned last (ophthalmic uses).

The polymers according to the invention are also suitable for use as a corneal implant or artificial cornea; and furthermore as cell growth substrates, as material for attachment and culture of animal cells in vitro and in vivo, as medical implants, for example implantable semi-permeable membrane materials, as tissue implants for cosmetic surgery, as an implant which comprises cells which secrete hormones, for example pancreatic islet cells, as a chest implant or as an artificial joint and the like.

The present invention therefore furthermore relates to a corneal implant which is produced from a polymer described above. Such a corneal implant can be produced by the same process as has been described above for the production of contact lenses. Corneal implants can be implanted by conventional surgical processes, for example under, into or through the epitheleal tissue of the cornea or into the stroma of the cornea or into other tissue layers of the cornea. Such implants can change the optical properties of the cornea, for example in the sense of correction of a visual deficit and/or by changing the appearance of the eye, for example the coloration of pupils. A corneal implant can include the region over the optical axis which covers the pupil on implantation and imparts the ability to see, and furthermore the region which surrounds the periphery of the optical axis. The implant can have the same visual properties over the entire region.

It has been found that the through-flow of high molecular weight components of tissue fluid, for example of proteins or glycoproteins, for example growth factors, peptides, hormones or proteins which are responsible for transportation of essential metal ions through a corneal implant, in particular between the epitheleal cells and stroma cells and even behind the endothelial layer, is important both for survival of tissue and for the viability of tissue outside and inside a corneal implant. A corneal implant is therfore preferably produced with a porosity which is sufficient to allow through fluid components of tissue having a molecular weight of greater than 10,000 Dalton, a through-flow of components of tissue fluid being ensured, in addition to a through-flow of low molecular weight nutrient components or metabolites, for example glucose, fats or amino acids, or respiratory gases between cells on both sides of an implant.

The porosity of a corneal implant is either determined by the polymer material itself from which it is produced or, on the other hand, pores can additionally be incorporated into a polymer according to the invention, in particular by one of the numerous known processes which are described, for example, in WO 90/07575, WO 91/07687, U.S. Pat. No. 5,244,799, U.S. Pat. No. 5,238,613, U.S. Pat. No. 4,799,931 or U.S. Pat. No. 5,213,721.

Regardless of the method with which the required porosity of an implant according to the invention is developed, an implant preferably has a porosity which is sufficient to allow through proteins and other biological macromolecules having a molecular weight up to or greater than 10,000 Dalton, for example a molecular weight of 10,000–1,000,000 Dalton, but is not so large that whole cells can pass through and can penetrate into the region over the optical axis of the implant. Where permeability of the implant is rendered possible by pores, the region over the optical axis comprises a large number of pores, the number of which should not be limited but should be sufficient to allow free through-flow of tissue components between the outer and the inner region of an implant. The pores which lie above the region of the optical axis preferably cause no scatter of visible light to an extent which would cause problems in respect of correction of vision. The term pore above and below is understood as meaning a pore which has no geometric restrictions and has either a regular or an irregular morphology. Statement of a pore size does not mean that all pores have the same diameter. Rather, this is an average diameter.

In the region outside the optical axis, the corneal implant can have the same porosity as in the region over the optical axis. This peripheral region of an implant which surrounds the region of the optical axis is also called a skirt, but in contrast to the region of the optical axis can allow corneal cells to grow in, whereupon the implant is anchored to the eye.

The porosity in the skirt can also be an independent feature of the material from which the skirt is produced. If the skirt is made of the same material as the material over the optical axis, pores of different diameter can be incorporated on the one hand on the skirt and on the other hand over the optical axis. On the other hand, the skirt can be produced from a different material to the material over the optical axis, in which case, as stated above, the porosity in the skirt should be greater than that over the optical axis. A skirt preferably comprises an optically clear polymer such as one over the optical axis; however, the skirt can also comprise an optically non-clear material, or it is produced from porous material which is optically non-clear.

A polymer according to the invention can assist colonization with tissue cells, such as, for example, vascular endothelial cells, fibroplasts or cells formed in bone, it not being necessary for a specific nature of the surface to be present in order to stimulate cell adhesion and cell growth. This is advantageous, since the process costs can be kept low. On the other hand, a polymer according to the invention can be modified on its surface by a known technique, for example plasma treatment of a surface by means of radiofrequency corona discharge, for example as described in U.S. Pat. No. 4,919,659 or in WO 89/00220, or by irradiation or with a chemical treatment.

A polymer according to the invention can be coated on the surface with one or with several components, for example to promote the growth of tissue. Such materials are, for example, fibronectin, chondroitin sulfate, collagen, laminin, cell fixing proteins, globulin, chondronectin, epidermal growth factors, muscle fibre proteins and/or derivatives thereof, and active fragments and mixtures thereof. Fibronectin, epidermal growth factors and/or derivatives thereof and active fragments and mixtures thereof are especially useful. If necessary, such a surface coating can also be carried out after a surface modification described above. A polymer according to the invention can advantageously combine several of the properties mentioned in itself, for example fixing to cells with good biostability and resistance to deposits.

The mechanical properties of a polymer according to the invention are suitable for use as a corneal implant, the material preferably having an E modulus of 0.5–10 MPa. The E modulus mentioned imparts to a corneal implant a suitable flexibility for allowing insertion into the eye, for example over the region of the Bowman's membrane.

A polymer according to the invention can furthermore be used as a cell growth substrate, for example as a cell culture apparatus, e.g. tableware, bottles, dishes and the like, and furthermore in biological reactors, for example in the preparation of valuable proteins and other cell culture components.

The examples described below serve to further illustrate the present invention; however, they are not intended to limit these in their scope in any manner. Temperatures are stated in degrees Celsius.

EXAMPLE A1

Preparation of:

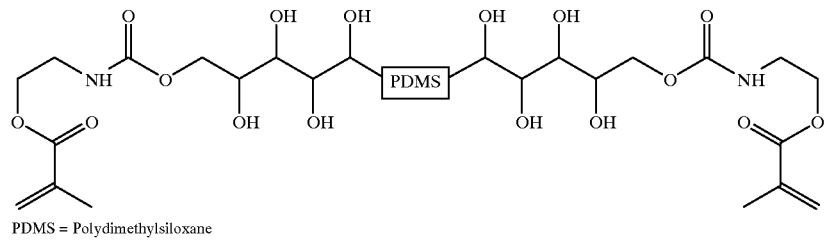

PDMS = Polydimethylsiloxane

Reaction of α,ω-bis-aminopropyl-dimethylpolysiloxane with D(+)gluconic acid δ-lactone Before the reaction, the amino-functionalized polydimethylsiloxane employed for the synthesis (X-22–161-C, Shin Etsu, JP) was finely dispersed in acetonitrile, extracted and then subjected to molecular distillation.

The following reactions take place with exclusion of $H_2O$. 200 g of purified amino-functionalized polydimethylsiloxane (0.375 meq of $NH_2$/g; $M_n$(VPO) 3400–3900 (VPO, Vapour Pressure Osmometry)), dissolved in 200 ml of absolute THF, are slowly added dropwise to a suspension of 13.35 g (75 mmol) of D(+)gluconic acid δ-lactone in 50 ml of absolute THF and the mixture is stirred at 40° C. for about 24 hours until the lactone has reacted completely. (Monitoring of the reaction by thin layer chromatography (TLC): silica gel; i-propanol/H$_2$O/ethyl acetate 6:3:1; staining with Ce(IV) sulfate/phosphoromolybdic acid solution (CPS reagent)). After the reaction, the reaction solution is concentrated to dryness and the residue is dried under 3 Pa (0.03 mbar) for 48 hours. 213.3 g of α,ω-bis(3-gluconamidopropyl)-poly-dimethylsiloxane are obtained. Titration of the amino groups with perchloric acid shows a conversion of the amino groups of more than 99.8%.

Reaction of α,ω-bis-3-gluconamidopropyl-dimethylpolysiloxane with IEM

The product obtained above (213.3 g) is dissolved in 800 ml of absolute THF and the solution is heated to 40° C. with the addition of catalytic amounts of dibutyltin dilaurate (DBTDL). 14 g (90 mmol) of IEM in 20 ml of absolute THF are added dropwise to this solution over a period of about 4 hours. This corresponds to a concentration of 1.2 equivalents of IEM per gluconamide unit. The reaction is carried out in the course of 48 hours (monitoring of the reaction by IR spectroscopy detection of the NCO bands). The reaction solution is concentrated and the product is dried in a brown glass flask under 3 Pa (0.03 mbar) for 24 hours, while cooling with ice. 227.2 g of a colourless rubber-elastic product of high optical transparency remain.

EXAMPLES A2–A7

Further amino propyl-dimethylpolysiloxanes (PDMS) are reacted with a different amount of gluconolactone and concentrations of IEM analogously to Example A1. The examples are summarized in Table 1.

TABLE 1

| | | | | Amount of batch | | |
|---|---|---|---|---|---|---|
| | PDMS | | | PDMS g (mmol of NH$_2$) | GLA g (mmol) | IEM g (mmol) |
| Ex. Name | Type | M$_n$ | NH$_2$* | | | |
| A1 X-22-161-C | term | 3400 | 2 | 200 (75) | 13.4 (75) | 14.0 (90.0) |
| A2 X-22-161-C | term | 3400 | 2 | 200 (74) | 13.4 (75) | 25.7 (165.0) |
| A3 X-22-161-C | term | 3400 | 2 | 200 (75) | 13.4 (75) | 29.2 (187.5) |
| A4 PS 813 | pen | 1200 | 1 | | | |
| A5 GP 4 | pen | 3150 | 2.6 | | | |
| A6 GP 6 | pen | 5960 | 3 | | | |
| A7 KP 8003 | pen | 9700 | 4.7 | 200 (98) | 17.5 (98) | 18.2 (117.4) |

Legend:
X-22-161-C and KF 8003 are products from Shin Etsu (Japan), PS 813 is a product from Petrarch-Hüls, GP4 and GP6 are products from Genesee.
*Amino groups per macromer chain
GLA: D (+) gluconic acid δ-lactone
term: terminal
pen: pendent

EXAMPLE A8

The reaction is carried out in accordance with Example A1, but instead of D(+)gluconic acid δ-lactone, 75 mmol of lactobionic acid 1,5-lactone, suspended in 50 ml of absolute THF, are added dropwise to a solution of amino-functionalized polydimethylsiloxane (X-22-161-C) in 180 ml of absolute THF and 20 ml of DMSO (pure, 99%). Titration of the amino groups with perchloric acid indicates a reaction conversion of 99% (<0.01 meq of NH$_2$/g). Here also, a colourless optically clear macromer is obtained.

EXAMPLE A9 and A10

The reactions are carried out analogously to Example A1. However, the catalyst necessary for addition of the isocyanate onto the hydroxyl groups is varied. Instead of DBTDL, catalytic amounts of 1,4-diazabicyclo[2.2.2]octane (DABCO) or 4-dimethylaminopyridine (DMAP) are added and the reaction is continued as described under Example A1. In both cases, an optically clear, colourless rubber-elastic macromer results in a manner corresponding to Example 1.

EXAMPLE A11

The reaction is carried out analogously to Example A1. In a manner corresponding to Example A8, 0.1 mol of lactobionic acid 1,5-lactone is suspended in 50 ml of absolute THF and the suspension is added dropwise to a solution of amino-functionalized polydimethylsiloxane (KF-8003) in 180 ml of absolute THF and 20 ml of DMSO (pure, 99%). The reaction time is increased to about 48 hours. A residual content of 0.07 meq of NH$_2$/g can be detected, and is reacted completely by addition of the corresponding molar amount of D(+)gluconic acid 5-lactone to the reaction solution. The colourless highly transparent product has a residual content of amino groups of <0.01 meq/g.

EXAMPLE A12

Preparation of:

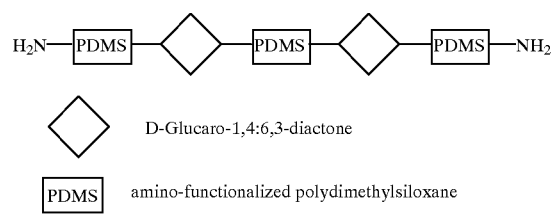

52.09 g (9.78 mmol) of purified amino-functionalized polydimethylsiloxane (X-22-161-C, Shin Etsu JP), dissolved in 110 ml of absolute THF, are initially introduced into the reaction vessel under an inert gas atmosphere, and 1.14 g (6.52 mmol) of D-glucaro-1,4:6,3-dilactone, dissolved in 20 ml of absolute THF, are added. The reaction solution is stirred at room temperature for 15 hours and then worked up in a manner corresponding to Example A1. The amine content is 0.134 meq/g.

The terminal amino groups of the resulting penta-block macromer are reacted with gluconolactone in the following reaction step. 41.84 g (5.146 meq of NH$_2$) of the above macromer and 0.917 g (5.15 mmol) of D(+)gluconic acid δ-lactone are suspended in 300 ml of absolute THF and the suspension is stirred under nitrogen at 40° C. for 18 hours. The filtered solution is then concentrated and the residue is dried under 3 Pa (0.03 mbar) for 48 hours. A highly viscous optically clear substance having a residual content of amino groups of 0.013 meq/g results.

Preparation of an amino- and perfluoroalkyl-functionalized polydimethylsiloxane:

EXAMPLE A13

3.0 ml of absolute toluene are added to 15 g of poly (dimethylsiloxane-co-methylhydrosiloxane) [Bayer Silopren U-230; 10,000 g/mol; 2.3 mmol of Si—H/g], and 1.72 g (9.2 mmol) of allylphthalimide [CAS Reg. No. 5428-09-1] are then added. The mixture is frozen several times and the flask evacuated and then brought to room temperature again. The flask is then let down with argon. 0.7 ml of a 0.005 molar solution of Lamoreaux catalyst (prepared in accordance with U.S. Pat. No. 3,220,972, General Electric) in absolute toluene (100 ppm of Pt/mol of Si—H) is added and the mixture is heated to 80° C. After a reaction time of half an hour, a colourless, clear to slightly cloudy solution, the $^1$H-NMR spectrum of which no longer shows resonances of allylic hydrogen atoms, is obtained.

Thereafter, 6.2 g (15.3 mmol) of degassed allyl 1H,1H, 2H,2H-perfluorooctyl ether are slowly added and the mixture is stirred at 80° C. for 2 hours. A $^1$H-NMR spectrum now shows a severely weakened resonance of the Si—H function at 4.6 ppm and an intense resonance at 0.5 ppm, which originates from Si-CH$_2$ hydrogen atoms.

3.0 ml of 1-hexene are then added in order to react the remaining excess of Si—H groups, which could otherwise cause crosslinking of the polymer when air later has access. The mixture is further stirred at 80° C. for another half an hour. The reaction mixture is then left to stand overnight. The product is purified over a silica gel column with hexane/ethyl acetate (3:2), the solvent is stripped off and the macromer is dried under a high vacuum. A colourless, clear, viscous product is obtained. The macromer purified in this way is taken up in 20 ml of hexane, 20 ml of methylamine [33% in ethanol] are added and the mixture is heated to 40° C. After 10–15 minutes, a white voluminous precipitate separates out. After 30 minutes, the suspension is cooled and filtered and the precipitate is washed with a little hexane. The filtrate is evaporated and the residue is then dried under a high vacuum. Thereafter, the content of amino groups is determined by titrimetry (perchloric acid). The resulting macromer is clear and viscous. The amino group content is 78.6% of theory. The total yield of macromer after the chromatographic purification is 75%.

Preparation of a gluconamide:

17.3 g (corresponding to an amine content of 5.4 meq) of this aminoalkyl-substituted product are dissolved in 20 ml of dried THF. The solution is repeatedly frozen, degassed and let down with argon. All the following operations are carried out in an argon atmosphere. 712 mg of D(+)-gluconic acid δ-lactone (4 mmol) are then added. Because of the low solubility of the lactone, a suspension is initially obtained. After stirring overnight at 50° C., the solution is clear and the lactone has been used completely. The stoichiometric remaining amount of D(+)-gluconic acid 8-lactone (260 mg, 1.46 mmol) is then added and the mixture is stirred again at 50° C. overnight. A trace of unreacted lactone is observed. Completion of the reaction is monitored by means of thin layer chromatography on silica gel plates with the mobile phase 1-propanol/ethyl acetate/water (6:1:3). The silica gel plates are developed by means of Ce(IV) sulfate/phosphoromolybdic acid solution. Subsequent titration on amino groups yields a residual amino content of <0.1%. After filtration and removal of the solvent by distillation, a highly viscous clear macromer with 0.295 mequivalent of gluconamide per gram of macromer is obtained.

EXAMPLE B1

Before the polymerization, the acrylates employed, isobutyl acrylate (IBA), N,N-dimethylacrylamide (DMA) and 3-methacryloyloxypropyl-tris(trimethylsilyloxy)silane (TRIS) are each freed from inhibitors by distillation. 0.32 g (2.76 mmol) of IBA, 0.80 g (8.1 mmol) of DMA and 1.44 g (3.4 mmol) of TRIS are weighed into a 50 ml round-bottomed flask and the flask is flushed with N$_2$ for half an hour, while cooling with ice. 1.44 g of macromer from Example A1 are transferred to a round-bottomed flask with a nitrogen attachment, degassed under 3 Pa (0.03 mbar) for 24 hours and then dissolved in 2.7 g of ethanol which has been flushed with N$_2$ for half an hour beforehand. The subsequent preparation of samples and the polymerization are carried out inside a glove box with exclusion of oxygen. The above monomer mixture and the macromer solution from Example A1 are mixed, with the addition of 0.012 g (0.21 mmol) of Darocure 1173® and the mixture is subjected to microfiltration (0.45 mm filter). 180 μl of this mixture are introduced into a polypropylene molding, which is then closed with an appropriate lid of polypropylene. The mixture is then irradiated with a UV-A mercury high pressure lamp in a nitrogen atmosphere in a UV oven equipped for this for 5 minutes. The lamps (5 each of the brand TLK 40W/1OR, Philips) are above and below the holder inserted. The irradiation intensity is 14.5 mW/cm$^2$.

The polypropylene molding is opened and the finished discs or lenses are removed by soaking by means of a solvent mixture of methylene chloride and ethanol (2:3). The lenses and discs are extracted in ethanol at room temperature in special polypropylene cages for 48 hours and then dried at 40° C. under 10 Pa (0.1 mbar) for 24 hours (autoclaving at 120° C., 30 minutes). The discs show an E modulus of 1.1 MPa, a permeability to oxygen of 183 barrer and a hardness (Shore A) of 53.

EXAMPLE B2–B12

Further polymers with different macromer starting compounds (Examples A1–A8) and a different nature and composition of the comonomers are prepared in a manner corresponding to Example B1 (composition in percentages by weight). Table 2 shows examples B2–B 12 and the properties of the resulting materials measured on discs.

TABLE 2

| Ex. | Water content % | Macromer wt. % | IBA wt. % | DMA wt % | TRIS wt. % | HFBA wt. % | DMEA wt. % | E modulus (MPa) | O$_2$Dk (barrer) | Hardness (Shore-A) |
|---|---|---|---|---|---|---|---|---|---|---|
| B2 | 4.6 | A2 36.0 | 8.0 | 20.0 | 36.0 | — | — | 1.0 | 198 | 42 |
| B3 | 9.1 | A2 35.0 | 5.0 | 20.0 | 35.0 | 5.0 | — | 1.2 | 190 | — |
| B4 | 12.1 | A2 35.0 | 20.0 | 20.0 | 25.0 | — | — | 0.4 | 123 | 33 |
| B5 | 13.7 | A3 32.8 | — | 30.0 | 37.2 | — | 30.0 | 1.1 | 135 | — |
| B6 | — | A3 32.8 | — | — | 37.2 | — | — | — | — | — |
| B7 | 19.9 | A3 32.9 | — | 34.3 | 32.7 | — | — | 0.7 | 84 | — |
| B8 | 25.1 | A3 39.3 | — | 34.3 | 36.4 | — | — | 0.9 | 72 | — |
| B9 | 17.5 | A3 35.7 | — | 34.3 | 30.0 | — | — | 0.7 | 100 | — |
| B10 | 23.4 | A3 33.3 | — | 33.3 | 33.4 | — | — | 0.7 | 96 | — |

TABLE 2-continued

| Ex. | Water content % | Macromer wt. % | IBA wt. % | DMA wt % | TRIS wt. % | HFBA wt. % | DMEA wt. % | E modulus (MPa) | O₂Dk (barrer) | Hardness (Shore-A) |
|---|---|---|---|---|---|---|---|---|---|---|
| B11 | — | A7 34.0 | 23.0 | — | 43.0 | — | — | 0.6 | 250 | 43 |
| B12 | 13.8 | A8 35.8 | 8.0 | 20.4 | 35.8 | — | — | 0.7 | — | 46 |

Legend:
IBA: Isobutyl acrylate
DMA: N,N-Dimethylacrylamide
TRIS: 3-Methacryloyloxypropyl-tris(trimethylsilyloxy)silane
HFBA: 2,2,3,4,4,4-Hexafluorobutyl acrylate
DMEA: 2-Dimethylaminoethyl acrylate

EXAMPLE B13

The synthesis of this polymer corresponds to Example B1 with the following comonomer composition: Example A3/TRIS/DMA, 32.8%/32.6%/34.2% (in percentages by weight) and an addition of 0.4% by weight of trimethylammonium-2-hydroxypropyl methacrylate hydrochloride (Blemer®QA, Nippon Oil Corp.). The polymer has a modulus of 0.9 MPa and a permeability to oxygen of ±2 barrer. The water content is 25.1% (after 30 minutes' autoclaving at 120° C.). For comparison, Example B7 has a water content of 20% with a very similar comonomer composition (no addition of Blemer®QA).

EXAMPLES B14–B29

The polymers are prepared analogously to Example B1, but the polymerization is carried out in bulk, which means without addition of ethanol. Table 3 shows the composition of the comonomers and the material properties of the polymers synthesized, measured on discs.

TABLE 3

| Example | Macromer (wt. %) | IBA (wt. %) | NVP (wt. %) | AN (wt. %) | EHA (wt. %) | OA (wt. %) | DA (wt. %) | E modulus (MPa) | O₂Dk (barrer) | Hardness (Shore A) |
|---|---|---|---|---|---|---|---|---|---|---|
| B14 | A1 (40) | 60 | — | — | — | — | — | 0.6 | 160 | 30 |
| B15 | A1 (63) | 37 | — | — | — | — | — | — | 290 | 52 |
| B16 | A1 (40) | — | — | — | 60 | — | — | 0.5 | 200 | 20 |
| B17 | A1 (54) | — | — | — | — | 46 | — | 0.7 | 224 | 47 |
| B18 | A1 (54) | — | — | — | — | — | 46 | — | 268 | 52 |
| B19 | A4 (40) | 60 | — | — | — | — | — | 0.6 | 150 | 40 |
| B20 | A4 (40) | — | — | — | 60 | — | — | 0.4 | 135 | 35 |
| B21 | A5 (40) | 60 | — | — | — | — | — | 1.5 | 90 | 55 |
| B22 | A5 (40) | — | — | — | 60 | — | — | 0.7 | 100 | 45 |
| B23 | A6 (40) | 60 | — | — | — | — | — | — | 120 | 55 |
| B24 | A6 (40) | — | — | — | 60 | — | — | — | 150 | 35 |
| B25 | A6 (53.5) | — | — | 8.6 | 37.9 | — | — | 0.9 | 260 | 51 |
| B26 | A7 (40) | 60 | — | — | — | — | — | 1 | 180 | 50 |
| B27 | A7 (40) | — | — | — | 60 | — | — | 0.6 | 170 | 40 |
| B28 | A7 (63) | 37 | — | — | — | — | — | 1.3 | 330 | 60 |
| B29 | A7 (41) | 23 | 24 | 12 | — | — | — | — | — | 68 |

OA: Iso-octyl acrylate
AN: Acrylonitrile
DA: Iso-decyl acrylate
NVP: 1-Vinyl-2-pyrrolidone
EHA: 2-Ethylhexyl acrylate

EXAMPLE B30

The polymerization is carried out in accordance with Example B1 but with the following changed comonomer composition: macromer A7/IBA/TRIS, 20%/19%/60% and 1% (in percentages by weight) of bis(3-methacryloyloxypropyl)tetramethyldisiloxane. An optically clear polymer with an E modulus of 0.4 MPa, a permeability to oxygen of 241 barrer and a hardness (Shore A) of 42 is obtained.

EXAMPLE B31

The polymerization is carried out analogously to Example B 1 with the following comonomer composition: macromer A1/IBA/TRIS, 37%/17%/43% (in percentages by weight). The polymerization is carried out in 1,4-dimethoxyethane instead of ethanol, and 3% of N-(m-isocyanato-p-toluoyl)-acryloyloxy ethylcarbamate (prepared according to the literature) are added as an additional crosslinking agent. The resulting polymer has a high optical transparency, a modululs of 0.7 MPa, a permeability to oxygen of 330 barrer and a Shore A hardness of 41.

EXAMPLE B32

5.0 g of the gluconamide-substituted macromer from Example A13 are dissolved in 5.0 g of absolute tetrahydrofuran. A mixture of 572 mg (3.69 mmol) of freshly distilled IEM and 0.5 g of absolute THF is added. This mixture is stirred at 50° C. for 24 hours. Thereafter, an IR spectrum shows no isocyanate absorption bands at 2250 cm$^{-1}$. The solvent is removed under a high vacuum, after which a clear, slightly yellowish and highly viscous intermediate results.

2.54 g of this are mixed with 1.7 g of absolute ethanol under an argon atmosphere. The mixture is repeatedly frozen and the flask evacuated and thawed again. Finally, the flask is let down with argon. In a second flask, 2.54 g of TRIS and 1.27 g of DMA are added together and the mixture is repeatedly frozen, evacuated and thawed again. It is then let down with argon. 30 mg of the photoinitiator Darocure®1173 are added and the mixture is frozen again, evacuated and thawed again and let down with argon. The two flasks are transferred to a glove box with an inert gas atmosphere. In this, the macromer solution and the comonomer mixture are mixed. The homogeneous solution is filtered and pipetted into polypropylene moldings for lenses or discs. The filled lens and disc moldings are irradiated with UV light (emission maximum at 360 nm) for 5 minutes. After the moldings have been opened, the crosslinked lenses and discs thus obtained are extracted in ethanol for 24 hours and then dried and subsequently equilibrated in distilled water. For sterilization, the lenses and discs are autoclaved in phosphate-buffered sodium chloride solution at 120° C. Clear lenses and discs are obtained. The permeability of the discs to oxygen is 120 barrer units and the absorption of water is 3.8% by weight.

EXAMPLE B33

A contact lens is prepared in a manner corresponding to example B1, using the example A3 macromer, with the following composition in percentages by weight:

Macromer A3: 33.3
DMA: 33.3
TRIS: 33.4

The lens has a Dk of about 94 and a water content of about 20.0 weight percent. The results are summarized in Table 4 for comparison.

EXAMPLE B34

Dried lenses prepared in accordance with the procedures described in example B33 are transferred into a plasma coating apparatus where the lenses are surface treated in a methane/air mixture. The apparatus and the plasma treatment process are both in accordance to the above indentified Yasuda disclosure.

The dried plasma-treated contact lenses are equilibrated in autoclave-resistant vials in phosphate-buffered physiological saline solution, and then autoclaved for 30 minutes at about 120° C. The plasma-treated autoclaved lens has a Dk of 90 and a water content of 21.5%. The results are summarized in table 4 for comparison.

TABLE 4

| Example | Surface treatment | Dk [barrer] | water content [wt. %] |
|---|---|---|---|
| B33 | untreated | 94 | 20.0 |
| B34 | plasma-treated | 90 | 21.5 |

EXAMPLE B35

In analogy to example B 1 the polymerization is carried out with the following comonomer composition in weight percent based on the total weight of the polymer Macromer A1: 33.3
DMA: 33.3
TRIS: 33.3

An optically clear polymer is obtained.

What is claimed is:

1. A macromonomer comprising at least one section of the formula (I)

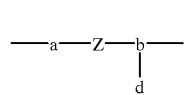

in which (a) is a polysiloxane segment derived from a compound of the formula (III)

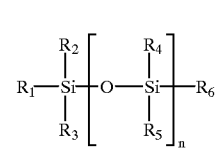

in which n is an integer from 5 to 500;

99.8–25% of the radicals $R_1$, $R_2$, $R_3$, $R_4$, $R_5$ and $R_6$ independently of one another are alkyl and 0.2–75% of the radicals $R_1$, $R_2$, $R_3$, $R_4$, $R_5$ and $R_6$ independently of one another are partly fluorinated alkyl, aminoalkyl, alkenyl, aryl, cyanoalkyl, alk—NH—alk—$NH_2$ or alk—$(OCH_2)_m$—$(OCH_2)_p$—$OR_7$, in which $R_7$ is hydrogen or lower alkyl, alk is alkylene, and m and p independently of one another are an integer from 0 to 10, one molecule of the formula (III) containing at least one primary amino or hydroxyl group;

wherein the radicals $R_4$ and $R_5$ are 1–50 times pendently aminoalkyl or hydroxyalkyl;

(b) is a polyol segment derived from a carbohydrate, carbohydrate monolactone, carbohydrate dilactone, a 1,3-polyol, or a polyvinyl alcohol, Z is a segment formed by a condensation reaction and is (c) or a group $X_1$, in which segment (c) is defined as $X_2$—R—$X_2$, in which R is a bivalent radical of an organic compound having up to 20 C atoms and each $X_2$ independently of the other is a bivalent radical which contains at least one carbonyl group, and in which $X_1$ is defined as $X_2$, and in which (d) is a radical of the formula (II)

$$X_3\text{—}L\text{—}(Y)_k\text{—}P_1 \qquad (II)$$

in which $P_1$ is a group which can be polymerized by free radicals;

Y and $X_3$ independently of one another are a bivalent radical which contains at least one carbonyl group;

k is 0 or 1; and

L is a bond or a divalent radical having up to 20 C atoms of an organic compound.

2. A macromer according to claim 1, in which a polysiloxane segment (a) is linked a total of 1–50 times via a group Z with a segment (b) or another segment (a), Z in an a-Z-a sequence always being a segment (c).

3. A macromer according to claim 1, in which a polysiloxane segment is derived from a compound of the formula (III) in which the radicals $R_1$, $R_2$, $R_3$, $R_4$, $R_5$ and $R_6$ are a total of 1–50 times independently either terminally or pendently aminoalkyl or hydroxyalkyl.

4. A macromer according to claim 1, in which a polysiloxane segment (a) is derived from a compound of the formula (III) in which 95–29% of the radicals $R_1$, $R_2$, $R_3$, $R_4$, $R_5$ and $R_6$ independently of one another are alkyl and 5–71% of the radicals $R_1$, $R_2$, $R_3$, $R_4$, $R_5$ and $R_6$ independently of one another are partly fluorinated alkyl, aminoalkyl, alkenyl, aryl, cyanoalkyl, alk—NH—alk—$NH_2$ or alk—$(OCH_2CH_2)_m$—$(OCH_2)_p$—$R_7$.

5. A macromer according to claim 1, in which n is an integer from 5 to 400.

6. A macromer according to claim 1, in which the two terminal radicals $R_1$ and $R_6$ are aminoalkyl or hydroxyalkyl.

7. A macromer according to claim 1, in which the radicals $R_4$ and $R_5$ are 2–30 times, pendently aminoalkyl or hydroxyalkyl.

8. A macromer according to claim 1, in which the radicals $R_1$, $R_2$, $R_3$, $R_4$, $R_5$ and $R_6$ are a total of 1–50 times independently both terminally and pendently aminoalkyl or hydroxyalkyl.

9. A macromer according to claim 1, in which Z is $X_1$.

10. A macromer according to claim 9, in which $X_1$ is a carbonyl group which is flanked not more than 2 times by —O—, —CONH—, —NHCO— or —NH—.

11. A macromer according to claim 10, in which $X_1$ is a carbonyl, ester, amide, urethane, urea or carbonate group.

12. A macromer according to claim 1, in which $X_2$ has the same meaning as $X_1$.

13. A macromer according to claim 10, in which $X_2$ is an ester, amide, urethane, carbonate or urea group.

14. A macromer comprising at least one section of the formula (I)

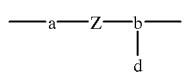   (I)

in which (a) is a polysiloxane segment;

(b) is a polyol segment derived from a mono-, di-, tri-, tetra-, oligo- or polysaccharide; from a lactone of an aldonic or uronic; or from glucuronic acid lactone, mannuronic acid lactone or iduronic acid lactone, Z is a segment formed by a condensation reaction and is (c) or a group $X_1$, in which segment (c) is defined as $X_2$—R—$X_2$, in which R is a bivalent radical of an organic compound having up to 20 C atoms and each $X_2$ independently of the other is a bivalent radical which contains at least one carbonyl group, and in which $X_1$ is defined as $X_2$, and in which (d) is a radical of the formula (II)

   (II)

in which $P_1$ is a group which can be polymerized by free radicals;

Y and $X_3$ independently of one another are a bivalent radical which contains at least one carbonyl group;

k is 0 or 1; and

L is a bond or a divalent radical having up to 20 C atoms of an organic compound.

15. A macromer according to claim 1, which is a compound of the formula (IV)

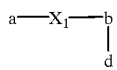   (IV)

in which the variables are as defined above.

16. A macromer of the formula (V)

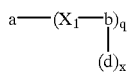   (V)

in which (a) is a polysiloxane segment containing q pendent ligands and in which x is 1 or 2, q has an average numerical value of 1–20, and in which the segments (b) in a macromer according to the formula (V) are linked in total (per molecule) with up to 20 polymerizable segments (d);

(b) is a polyol segment derived from a carbohydrate, carbohydrate monolactone, carbohydrate dilactone or a 1,3-polyol.

$X_1$ is a bivalent radical which contains at least one carbonyl group, and in which (d) is a radical of the formula (II)

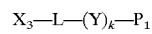   (II)

in which $P_1$ is a group which can be polymerized by free radicals;

Y and $X_3$ independently of one another are a bivalent radical which contains at least one carbonyl group;

k is 0 or 1; and

L is a bond or a divalent radical having up to 20 C atoms of an organic compound.

17. A macromer according to claim 1, containing a section of the formula (VI)

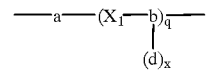   (VI)

in which a linear sequence is present, in which x is 0, 1 or 2, q has an average numerical value of 1–20, and in which the segments (b) in a macromer according to the formula (VI) are linked in total (per molecule) with up to 20 polymerizable segments (d).

18. A macromer of the formula (VII)

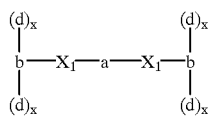   (VII)

in which (a) is a polysiloxane segment, x is 0, 1 or 2, and the average number of segments (d) per molecule of the formula (VII) is in the range from 2 to 5;

(b) is a polyol segment derived from a carbohydrate, carbohydrate monolactone, carbohydrate dilactone or a 1,3-polyol, $X_1$ is a bivalent radical which contains at least one carbonyl group, and in which (d) is a radical of the formula (II)

$$X_3\text{—}L\text{—}(Y)_k\text{—}P_1 \quad (II)$$

in which $P_1$ is a group which can be polymerized by free radicals;

Y and $X_3$ independently of one another are a bivalent radical which contains at least one carbonyl group;

k is 0 or 1; and

L is a bond or a divalent radical having up to 20 C atoms of an organic compound.

19. A macromer according to claim 1, in which a polyol segment (b) is derived from a polyol which carries no lactone group and the group Z is a segment (c).

20. A macromer according to claim 1, in which a polyol segment (b) is derived from a monosaccharide, polyvinyl alcohol (PVA) or cyclodextrin.

21. A macromer according to claim 1, in which a segment (b) carries at least one vinylic polymerizable segment (d), the segment (d) being linked via the bivalent radical $X_3$ thereof to an amino or hydroxyl group, of a segment (b), which hydroxyl group is reduced by a hydrogen atom.

22. A macromer according to claim 1, in which, per macromer molecule according to the invention, a vinylic polymerizable segment (d) is incorporated either terminally or pendently preferably 1–20 times.

23. A macromer according to claim 1, in which, per macromer molecule according to the invention, a vinylic polymerizable segment (d) is incorporated terminally and also pendently.

24. A macromer according to claim 1, in which $P_1$ is alkenyl, alkenylaryl or alkenylarylenealkyl having up to 20 C atoms.

25. A macromer according to claim 1, in which L is alkylene, arylene, a saturated bivalent cycloaliphatic group having 6 to 20 carbon atoms, arylenealkylene, alkylenearylene, alkyenearylenealkylene or arylenealkylenearylene.

26. A macromer according to claim 1, in which L is a bond.

27. A macromer according to claim 1, in which Y is a carbonyl, ester, amide or urethane group.

28. A macromer according to claim 1, in which k is 0.

29. A macromer according to claim 1, in which $X_3$ is a urethane, urea, ester, amide or carbonate group.

30. A macromer according to claim 1, in which a segment (d) is derived from acrylic acid, methacrylic acid, methacryloyl chloride, 2-isocyanatoethyl methacrylate (IEM), allyl isocyanate, vinyl isocyanate, the isomeric vinylbenzyl isocyanates or adducts of hydroxyethyl methacrylate (HEMA) and 2,4-tolylene diisocyanate (TDI) or isophorone diisocyanate (IPDI), in particular the 1:1 adduct.

31. A macromer according to claim 1, in which a segment (d) is incorporated either terminally or pendently or as a terminal/pendent mixture 5 times per molecule.

32. A macromer according to claim 1, in which R is alkylene, arylene, alkylenearylene, arylenealkylene or arylenealkylenearylene having up to 20 carbon atoms, a saturated bivalent cycloaliphatic group having 6 to 20 carbon atoms or cycloalkylenealkylenecycloalkylene having 7 to 20 carbon atoms.

33. A macromer according to claim 1, in which a segment (c) is derived from hexane 1,6-diisocyanate, 2,2,4-trimethylhexane 1,6-diisocyanate, tetramethylene diisocyanate, phenylene 1,4-diisocyanate, toluene 2,4-diisocyanate, toluene 2,6-diisocyanate, m- or p-tetramethylxylene diisocyanate, isophorone diisocyanate or cyclohexane 1,4-diisocyanate.

34. A macromer according to claim 1, in which the weight-average molecular weight of the macromer is in the range from about 300 to 30,000.

35. A macromer of the formula (VIII)

$$b\text{-}Z\text{-}a\text{-}\{c\text{-}a\}_r\text{-}(Z\text{-}b)_t \quad (VIII)$$

in which r is an integer from 1 to 10;

in which a linear (c-a) chain which may or may not be terminated by a segment (b) is present (t=1); wherein a segment (d) is bonded to at least one segment (b);

in which (a) is a polysiloxane segment;

(b) is a polyol segment derived from a carbohydrate, carbohydrate monolactone, carbohydrate dilactone, or a 1,3-polyol;

Z is a segment formed by a condensation reaction and is (c) or a group $X_1$, in which segment (c) is defined as $X_2\text{—}R\text{—}X_2$, in which R is a bivalent radical of an organic compound having up to 20 C atoms and each $X_2$ independently of the other is a bivalent radical which contains at least one carbonyl group, and in which X, is defined as $X_2$, and in which (d) is a radical of the formula (II)

$$X_3\text{—}L\text{—}(Y)_k\text{—}P_1 \quad (II)$$

in which $P_1$ is a group which can be polymerized by free radicals;

Y and $X_3$ independently of one another are a bivalent radical which contains at least one carbonyl group;

k is 0 or 1; and

L is a bond or a divalent radical having up to 20 C atoms of an organic compound.

36. A macromer of the formula (IX)

$$b\text{-}Z\text{-}a\text{-}\{c\text{-}a\text{-}(Z\text{-}b)_t\}_r \quad (IX)$$

in which the sequence (c-a)-(Z-b)$_t$ hangs pendently r times on the segment (a) and may or may not be terminated by a segment (b);

in which t is an integer from 1 to 10;

t is 0 or 1;

wherein a segment (d) is bonded to at least one segment (b);

in which (a) is a polysiloxane segment;

(b) is a polyol segment derived from a carbohydrate, carbohydrate monolactone, carbohydrate dilactone or a 1,3-polyol;

Z is a segment formed by a condensation reaction and is (c) or a group $X_1$, in which segment (c) is defined as $X_2\text{—}R\text{—}X_2$, in which R is a bivalent radical of an organic compound having up to 20 C atoms and each $X_2$ independently of the other is a bivalent radical which contains at least one carbonyl group, and in which $X_1$ is defined as $X_2$, and in which (d) is a radical of the formula (II)

$$X_3\text{—}L\text{—}(Y)_k\text{—}P_1 \quad (II)$$

in which $P_1$ is a group which can be polymerized by free radicals;

Y and $X_3$ independently of one another are a bivalent radical which contains at least one carbonyl group;

k is 0 or 1; and

L is a bond or a divalent radical having up to 20 C atoms of an organic compound.

37. A macromer according to claim 1, which is a compound of the formula (X)

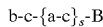  (X)

in which s is an integer from 1 to 10;

B is a segment (a) or (b);

wherein a segment (d) is bonded to at least one segment (b).

38. A macromer according to claim 1, which is a compound of the formula (XI)

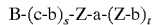  (XI)

wherein the macromer has a linear structure, and in which s is an integer from 1 to 10;

B is a segment (a) or (b); wherein a segment (d) is bonded to at least one segment (b);

and t is 0 or 1.

39. A macromer according to claim 1, in which the ratio of the number of segments (a) and (b) is in a range of (a):(b)=3:4, 2:3, 1:2, 1:1, 1:3 or 1:4.

40. A macromer according to claim 1, in which the total sum of segments (a) and (b) or, where appropriate, (a) and (b) and (c) is in a range from 2 to 50.

41. Macromer of the formula (IV)

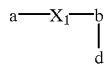  (IV)

in which (a) is a polysiloxane segment is derived from a compound of the formula

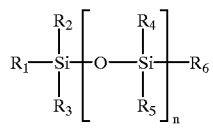  (III)

in which 95–29% of the radicals $R_1$, $R_2$, $R_3$, $R_4$, $R_5$ and $R_6$ independently of one another are lower alkyl, 5–71% of the radicals $R_1$, $R_2$, $R_3$, $R_4$, $R_5$ and $R_6$ independently of one another are partly fluorinated alkyl, aminoalkyl or hydroxyalkyl, and n is an integer from 5 to 400;

the polyol segment (b) is derived from a carbohydrate, carbohydrate monolactone or carbohydrate dilactone;

(d) is a radical of the formula (II): $X_3$—L—$(Y)_k$—$P_1$, in which $P_1$ is alkenyl, $X_3$ is a urethane or urea group, Y is a carbonyl, ester or amide group, k is 0 or 1, and L is a bond or alkylene; and $X_1$ is an ester, amide, urethane or urea group.

42. Macromer according to claim 35, wherein the variables are defined as follows:

a polysiloxane segment (a) is derived from a compound of the formula (III)

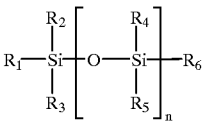  (III)

in which 95–29% of the radicals $R_1$, $R_2$, $R_3$, $R_4$, $R_5$ and $R_6$ independently of one another are lower alkyl, 5–71% of the radicals $R_1$, $R_2$, $R_3$, $R_4$, $R_5$ and $R_6$ independently of one another are partly fluorinated alkyl, aminoalkyl or hydroxyalkyl, and n is an integer from 5 to 400;

polyol segment (b) is derived from a 1,3-polyol, carbohydrate, carbohydrate monolactone or carbohydrate dilactone, with the provisio that segment (b) is derived from a polyol which carries no lactone group if the group Z is a segment (c);

Z is a segment (c) or $X_1$, wherein $X_1$ is an ester, amide, urethane or urea group, and wherein segment (c) represents $X_2$—R—$X_2$, in which R is alkylene, arylene, alkylenearylene or arylenealkylene having up to 14 carbon atoms, or a saturated bivalent cycloaliphatic group having 6 to 14 carbon atoms, and $X_2$ is an amide, urethane or urea group;

(B) is a segment (a) or a segment (b) with the above mentioned definitions; and (d) is a radical of the formula (II): $X_3$—L—$(Y)_k$—$P_1$, which is up to 15 times terminally and/or pendently attached to a segment (b), and wherein $P_1$ is alkenyl, $X_3$ is a ester, amide, urethane or urea group, Y is a carbonyl, ester or amide group, k is 0 or 1, and L is a bond or alkylene.

43. A process for the preparation of a macromer, which comprises first reacting a polysiloxane containing at least one primary amino- or hydroxyalkyl group with a carbohydrate lactone, an amide or ester bond being formed and a compound of the formula (XIIa) or (XIIb) being formed

  (XIIa)

  (XIIb)

in which (a) is a polysiloxane segment;

(b) is a polyol segment derived from a carbohydrate, carbohydrate monolactone, carbohydrate dilactone or a 1,3-polyol;

Z is a group $X_1$, wherein $X_1$ is a bivalent radical which contains at least one carbonyl group, and q is an average numerical value of 1–20;

after which a compound (XIIa) or (XIIb) is reacted with precursors of (d), an unsaturated polymerizable compound of the formula (XIII)

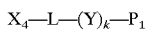  (XII)

in which $X_4$ is a group which is coreactive with a hydroxyl or amino group of segment (b), in which $P_1$ is a group which can be polymerized by free radicals;

Y is a bivalent radical which contains at least one carbonyl group, k is 0 or 1, and L is a bond or a divalent radical having up to 20 C atoms of an organic compound;

after which a macromer according to the formula (IV) or (V) is formed

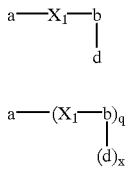  (IV)

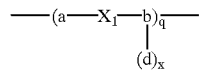  (V)

in which the segments (d) are incorporated terminally or pendently, and x is 0, 1 or 2.

44. A process for the preparation of a macromer as defined in claim 43, which comprises reacting a polysiloxane (a) which contains terminal primary amino- or hydroxyalkyl groups with a carbohydrate dilactone to give linear structures of the formula (XIV)

$-(a-X_1-b)_q-$  (XIV)

in which q is an average numerical value of 1–20, after which a compound of the formula (XIV) is reacted with a compound of the formula (XIII) analogously to the above process to give a macromer of the formula (VI)

  (VI)

in which x is 0, 1 or 2.

45. A process for the preparation of a macromer as defined in claim 43, which comprises first reacting a polysiloxane (a) which contains terminal primary amino- or hydroxyalkyl groups with a bifunctional compound of the formula (XV)

$X_4-R-X_4$  (XV)

in which $X_4$ is a group which is coreactive with a hydroxyl or amino group of segment (a), and an $X_2$ group of a segment (c) being formed from such a reaction, in which $R_{10}$ is alkyl, or aryl which is unsubstituted or substituted by lower alkyl or lower alkoxy, after which this intermediate is reacted with a polyol which carries no lactone group to give a compound of the formula (XVI)

b-c-{a-c}$_s$-b  (XVI)

in which s is an integer from 1 to 10, after which the compound of the formula (XVI) is reacted with a compound of the formula (XIII) to give a macromer of the formula (X)

b-c-{a-c}$_s$-B  (X)

in which s is an integer from 1 to 10, preferably from 1 to 7, and in particular from 1 to 3; and B is a segment (a) or (b).

46. A process for the preparation of a macromer as defined in claim 43, which comprises reacting a bifunctional compound of the formula (XV)

$X_4-R-X_4$  (XV)

with an excess of polysiloxane (a) to give an -a-(c-a)r-sequence, in which the above meanings apply, after which, in a second step, the intermediate is reacted with a polyol which carries no lactone to give a compound of the formula (XVII)

b-Z-a-{c-a}$_r$-Z-b  (XVII)

after which the compound (XVII) is reacted with the compound (XIII) to give a macromer of the formula (VIII)

b-Z-a-{c-a}$_r$(Z-b)$_t$  (VIII)

in which r is an integer from 1 to 10;
in which a linear (c-a) chain, which may or may not be terminated by a segment (b), is present (t=1).

47. A process for the preparation of a macromer as defined in claim 43, which comprises reacting, in a first step, a carbohydrate lactone with a compound of the formula (XIII), the lactone function being retained, after which the intermediate is reacted with a polysiloxane containing at least one amino or hydroxyl group to give a compound of the formula (IV) or (V)

  (IV)

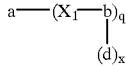  (V)

in which q is 1 or 2, and x is 0, 1 or 2.

48. A polymer comprising a polymerization product of at least one macromer as defined in claim 1 and, if appropriate, of at least one vinylic comonomer (a).

49. A polymer according to claim 48, in which the weight content of the macromer is in the range from 100 to 0.5%, based on the total weight of the polymer.

50. A polymer according to claim 48, in which comonomer (a) is absent.

51. A polymer according to claim 48, in which comonomer (a) is hydrophilic or hydrophobic or a mixture of both.

52. A polymer according to claim 48, in which comonomer (a) is chosen from $C_1-C_{18}$alkyl and $C_3-C_{18}$cycloalkyl acrylate and methacrylate, $C_3-C_{18}$alkylacrylamide and -methacrylamide, acrylonitrile, methacrylonitrile, vinyl $C_1-C_{18}$alkanoate, $C_2-C_{18}$alkene, $C_2-C_{18}$haloalkene, styrene, lower alkyl styrene, lower alkyl vinyl ether, $C_2-C_{10}$perfluoroalkyl acrylate and methacrylate or correspondingly partly fluorinated acrylate and methacrylate, $C_3-C_{12}$perfluoroalkyl-ethyl-thio carbonylaminoethyl acrylate and methacrylate, acryloxy- and methacryloxy-alkylsiloxane, N-vinylcarbazole and $C_1-C_{12}$alkyl ester of maleic acid, fumaric acid, itaconic acid, and mesaconic acid.

53. A polymer according to claim 48, in which comonomer (a) is chosen from hydroxyl-substituted lower alkyl acrylate and methacrylate, acrylamide, methacrylamide, lower alkylacrylamide and -methacrylamide, ethoxylated acrylate and methacrylate, hydroxyl-substituted lower alkylacrylamide and -methacrylamide, hydroxyl-substituted lower alkyl vinyl ether, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl-4,4'-dialkyloxazolin-5-one, 2- and 4-vinylpyridine, vinylically unsaturated carboxylic acid having a total of 3 to 5 carbon atoms, amino-lower alkyl (where the term "amino" also includes quaternary ammonium), mono-lower alkylamino-lower alkyl and di-lower alkylamino-lower alkyl acrylate and methacrylate, and allyl alcohol.

54. A polymer according to claim 48, furthermore comprising at least one comonomer (b).

55. A polymer according to claim 54, in which comonomer (b) is chosen from allyl (meth)acrylate, lower alkylene glycol di(meth)acrylate, poly lower alkylene glycol di(meth)acrylate, lower alkylene di(meth)acrylate, divinyl ether, divinyl sulfone, di- or trivinylbenzene, tetramethylolpropane tri(meth)acrylate, pentaerythritol tetra(meth)acrylate, bisphenol A di(meth)acrylate, methylenebis(meth)acrylamide, triallyl phthalate or diallyl phthalate.

56. A Polymer which comprises the polymerization product of the following components in weight percent based on the total weight of the polymer:
   (1) 25–45% of a macromer of formula IV in accordance to claim 18, wherein the variables are defined as follows:
   a polysiloxane segment (a) is derived from a compound of the formula (III)

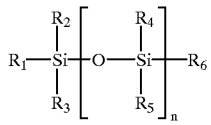

(III)

in which 95–29% of the radicals $R_1$, $R_2$, $R_3$, $R_4$, $R_5$ and $R_6$ independently of one another are lower alkyl, 5–71% of the radicals $R_1$, $R_2$, $R_3$, $R_4$, $R_5$ and $R_6$ independently of one another are partly fluorinated alkyl, aminoalkyl or hydroxyalkyl, and n is an integer from 5 to 400;
   a polyol segment (b) is derived from a carbohydrate, carbohydrate monolactone or carbohydrate dilactone;
   (d) is a radical of the formula (II): $X_3$—L—$(Y)_k$—$P_1$, in which $P_1$ is alkenyl, $X_3$ is a urethane or urea group, Y is a carbonyl, ester or amide group, k is 0 or 1, and L is a bond or alkylene; and
   $X_1$ is an ester, amide, urethane or urea group,
   (2) 25–75% of a hydrophobic monomer, and
   (3) 15–40% of a hydrophilic monomer.

57. Polymer which comprises the polymerization product of the following components in weight percent based on the total weight of the polymer:
   (1) 25–45% of a macromer of formula (VII) according to the definitions of claim 35, wherein the variables are defined as follows:

a polysiloxane segment (a) is derived from a compound of the formula (III) in which 95–29% of the radicals $R_1$, $R_2$, $R_3$, $R_4$, $R_5$ and $R_6$ independently of one another are lower alkyl, 5–71% of the radicals $R_1$, $R_2$, $R_3$, $R_4$, $R_5$ and $R_6$ independently of one another are partly fluorinated alkyl, aminoalkyl or hydroxyalkyl, and n is an integer from 5 to 400;
   a polyol segment (b) is derived from a polyol, carbohydrate, carbohydrate monolactone or carbohydrate dilactone, with the provisio that segment (b) is derived from a polyol which carries no lactone group if the group Z is a segment (c);
   Z is a segment (c) or $X_1$, wherein $X_1$ is an ester, amide, urethane or urea group, and wherein segment (c) represents $X_2$—R—$X_2$, in which R is alkylene, arylene, alkylenearylene or arylenealkylene having up to 14 carbon atoms, or a saturated bivalent cycloaliphatic group having 6 to 14 carbon atoms, and $X_2$ is an amide, urethane or urea group;
   (B) is a segment (a) or a segment (b) with the above mentioned definitions; and
   (d) is a radical of the formula (II): $X_3$—L—$(Y)_k$—$P_1$, which is up to 15 times terminally and/or pendently attached to a segment (b), and wherein $P_1$ is alkenyl, $X_3$ is a ester, amide, urethane or urea group, Y is a carbonyl, ester or amide group, k is 0 or 1, and L is a bond or alkylene,
   (2) 25–75% of a hydrophobic monomer, and
   (3) 15–40% of a hydrophilic monomer.

58. A molding comprising a polymer according to claim 48.

59. A molding comprising a polymer according to claim 48, wherein the surface of the molding is plasma treated in the presence of a $C_1$–$C_6$alkane and a gas which is selected from the group consisting of nitrogen, argon, oxygen, and mixtures thereof.

60. A molding according to claim 58, which is a contact lens.

61. A molding according to claim 58, which is a soft contact lens having a water content of 1–40%, based on the total weight of the molding.

62. A molding according to claim 58, which is a flexible contact lens which is permeable to gas and has a low water content (RGP).

63. A method comprising polymerizing and shaping a macromer as defined in claim 1 for the production of a molding.

64. A method comprising polymerizing and shaping a macromer as defined in claim 1 for the production of a contact lens.

* * * * *